(12) United States Patent
Abe et al.

(10) Patent No.: US 7,167,740 B2
(45) Date of Patent: Jan. 23, 2007

(54) MEASURING METHOD IN MAGNETIC RESONANCE IMAGING DEVICE AND MAGNETIC RESONANCE IMAGING DEVICE

(75) Inventors: Takayuki Abe, Matsudo (JP); Shigeru Watanabe, Ibaraki-ken (JP); Hirotaka Takeshima, Ryuugasaki (JP)

(73) Assignee: Hitachi Medical Corporation, Tokyo (JP)

( * ) Notice: Subject to any disclaimer, the term of this patent is extended or adjusted under 35 U.S.C. 154(b) by 506 days.

(21) Appl. No.: 10/433,736

(22) PCT Filed: Dec. 3, 2001

(86) PCT No.: PCT/JP01/10538

§ 371 (c)(1),
(2), (4) Date: Jun. 4, 2003

(87) PCT Pub. No.: WO02/45584

PCT Pub. Date: Jun. 13, 2002

(65) Prior Publication Data

US 2004/0027124 A1 Feb. 12, 2004

(30) Foreign Application Priority Data

Dec. 4, 2000 (JP) .............................. 2000-368220
Dec. 15, 2000 (JP) ............................. 2000-381171

(51) Int. Cl.
*A61B 5/05* (2006.01)

(52) U.S. Cl. ...................... 600/420; 600/410; 600/413; 600/431; 600/419; 324/307; 324/309; 324/306; 324/318

(58) Field of Classification Search ........ 324/306–309, 324/318; 600/407–410, 420, 431, 413, 419; 358/111

See application file for complete search history.

(56) References Cited

U.S. PATENT DOCUMENTS 4,885,537 A * 12/1989 Suzuki ....................... 324/309

(Continued)

FOREIGN PATENT DOCUMENTS

JP          6-343621         12/1994

(Continued)

OTHER PUBLICATIONS

Japanese Language International Search Report (and English-language translation thereof) in connection with corresponding International Application No. PCT/JP01/10538.

(Continued)

*Primary Examiner*—Brian L. Casler
*Assistant Examiner*—John F. Ramirez
(74) *Attorney, Agent, or Firm*—Cooper & Dunham LLP

(57) ABSTRACT

In a measuring space of the object (1), an essential measurement region (41, 61, 71, 81, 111, 131) having a center region of the measuring space and a plurality of peripheral measurement regions (42, 62, 63, 72, 82, 112, 132) which do not have any region overlapped with the essential measurement region are set. Then, the essential measurement region is combined with a selected peripheral portion of the plurality of the peripheral measurement regions to measure in a preceding manner a nuclear magnetic resonance signal from the object as data of the measuring space. The essential measurement region is combined with the peripheral measurement region of the plurality of the peripheral measurement regions which has not been selected in the preceding measuring step to measure a nuclear magnetic resonance signal from the object as data of the measuring space. Sequentially, the essential measurement region is combined with the peripheral measurement region having not been measured in a preceding measuring step to measure a nuclear magnetic resonance signal from the object. The data of the essential measurement region and the data of the peripheral measurement region thus measured is supplemented with the data of the peripheral measurement region measured in the preceding measuring step to generate data of the measuring space.

23 Claims, 15 Drawing Sheets

U.S. PATENT DOCUMENTS 5,713,358 A * 2/1998 Mistretta et al. ............ 600/420
5,830,143 A * 11/1998 Mistretta et al. ............ 600/420
6,556,856 B1 * 4/2003 Mistretta et al. ............ 600/420

FOREIGN PATENT DOCUMENTS

JP        10/5191       1/1998
JP        10-512482    12/1998

OTHER PUBLICATIONS

Keiji Fukui, et al., (1988) "An Investigation of Cerebral MR Angioimaging", Progress in CT, vol. 10, No. 2, pp. 133-142.

Charles L. Dumolulin, Ph.D, et al., (1986) "Magnetic Resonance Angiography", Radiology, pp. 717-720.

Charles L. Dumolulin, Ph.D., et al., (Jul./Aug. 1991), "Simultaneous Acquisition of Phase-Contrast Angiograms and Stationary-Tissue Images with Hadamard Encoding of Flow-induced Phase Shifts", JMRI pp. 399-404.

Norbert J. Pelc et al., (Jul./Aug. 1991), "Encoding Strategies for Three-Direction Phase-Contrast MR Imaging of Flow", JMRI, pp. 405-413.

William G. Bradley, "Flow Phenomena" in Magnetic Resonance Imaging edited by D.D. Stark et al. (1998) pp. 108-137.

"Basic Concepts" in 3D Contrast MR Angiography by M.R. Prince et al. (2d ed. 1998), pp. 3-39.

* cited by examiner

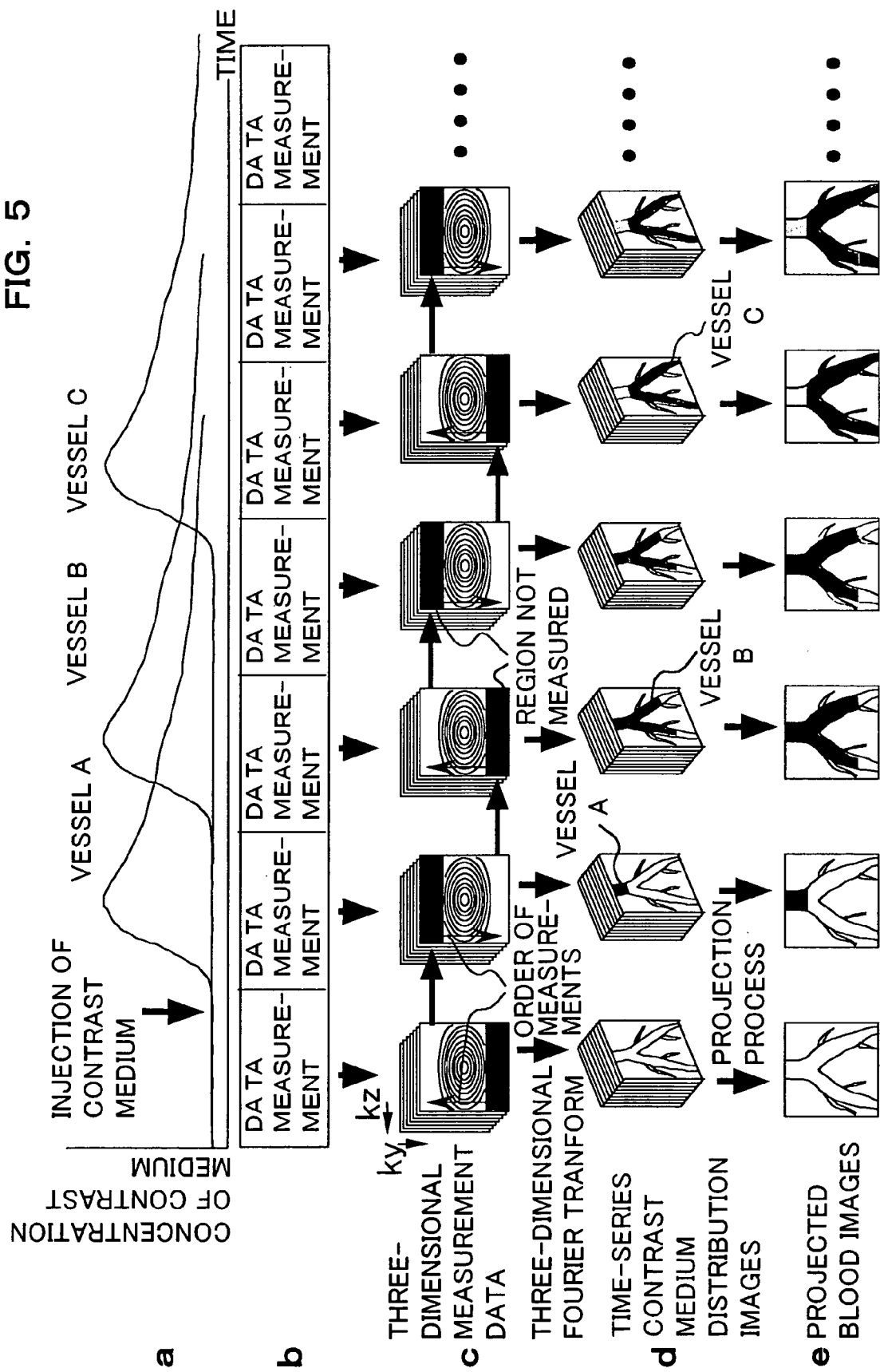

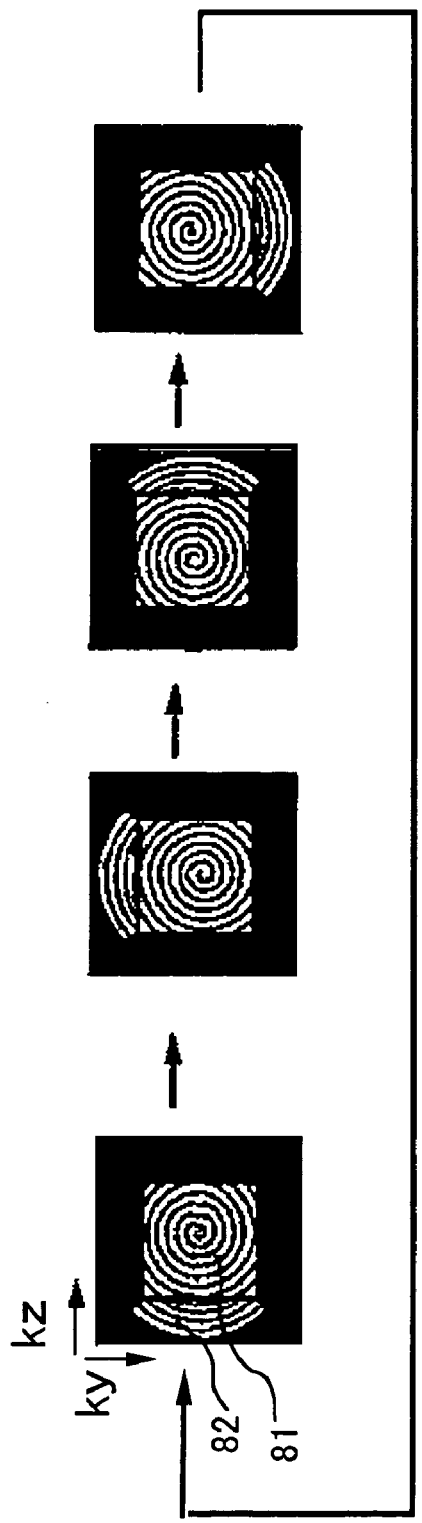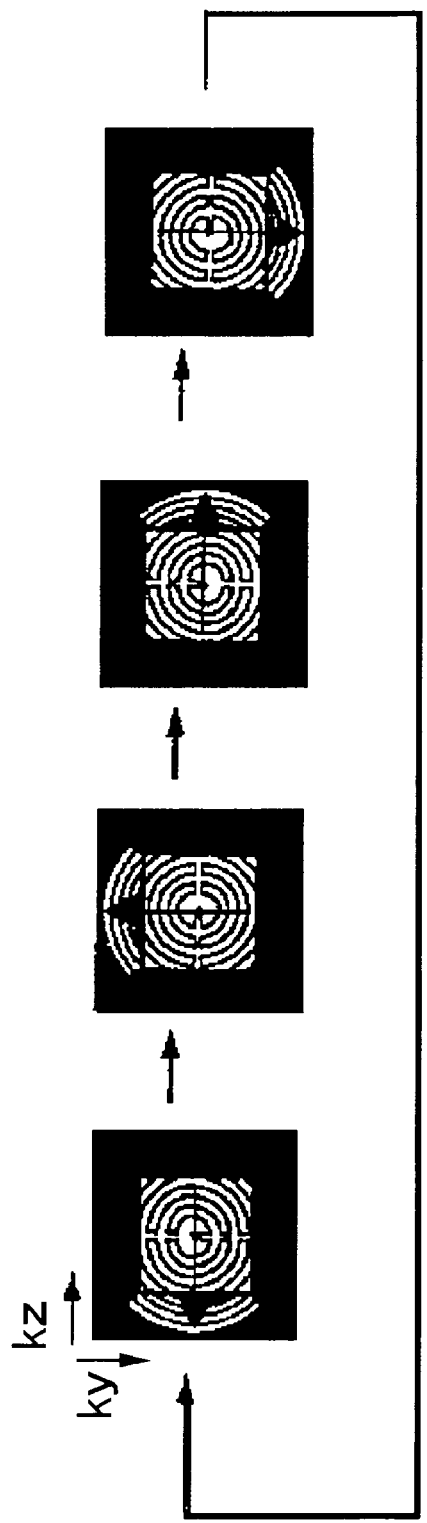

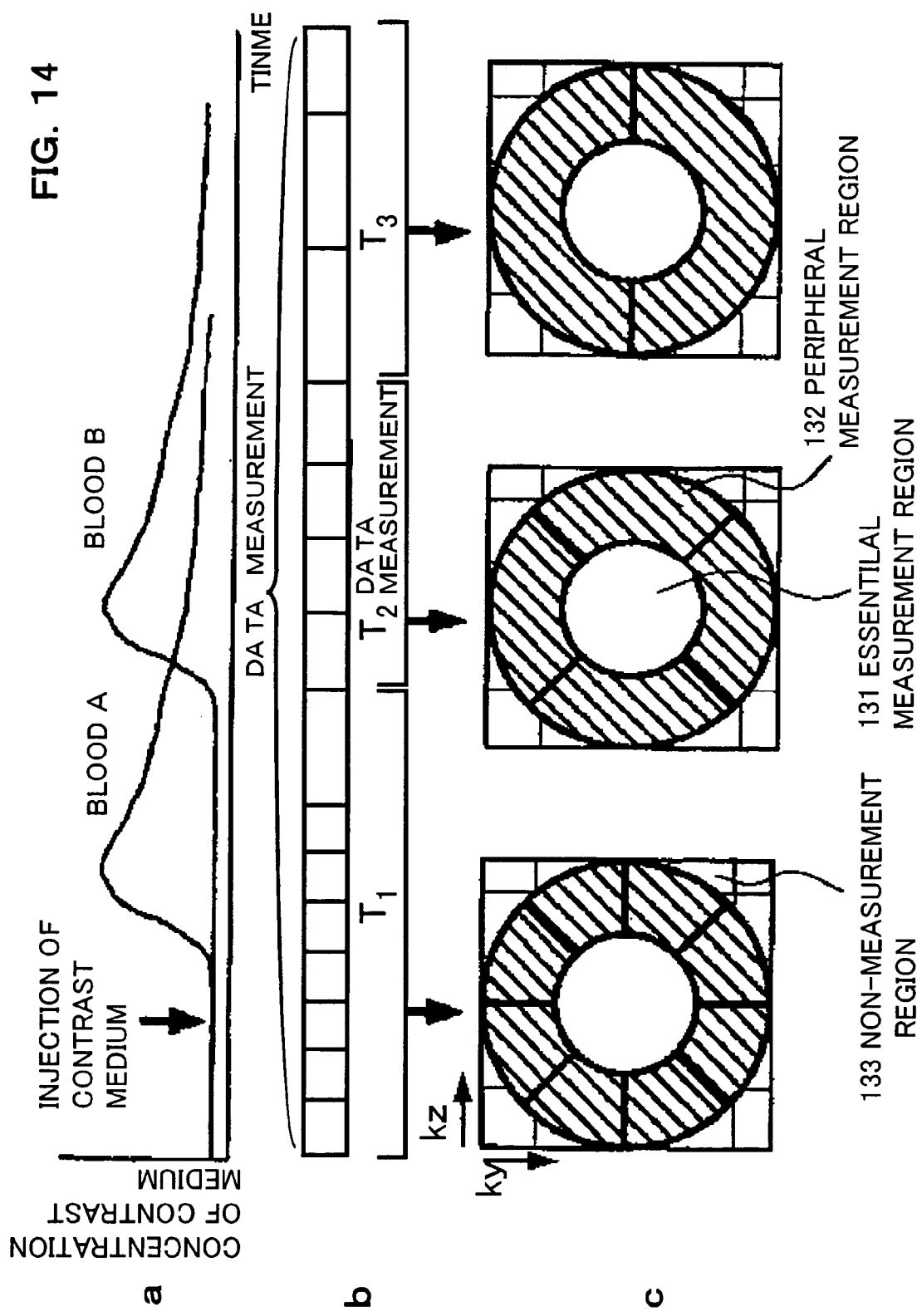

MEASURING METHOD IN MAGNETIC RESONANCE IMAGING DEVICE AND MAGNETIC RESONANCE IMAGING DEVICE

TECHNICAL FIELD

The present invention relates to a magnetic resonance imaging (MRI) apparatus which utilizes a nuclear magnetic resonance phenomenon to produce a tomographic image of an object to be examined, and more particularly, to a measuring method and apparatus suitable for dynamic magnetic resonance angiography imaging in a magnetic resonance imaging apparatus.

BACKGROUND ART

The MRI (magnetic resonance imaging) apparatus utilizes the NMR phenomenon to measure a density distribution, a relaxation time distribution, and the like of nuclear spins in a desired portion under testing of the object, and displays an image of a cross-section of an arbitrary portion of the object from the measured data.

The technology for producing a blood flow image utilizing such a magnetic resonance imaging apparatus is called MRA (magnetic resonance angiography). This MRA can be roughly classified into an approach which uses a contrast medium and an approach which does not use the contrast medium.

Here, a portion supplied with the contrast medium can receive a larger signal, as compared with a portion not supplied with the same, so that a vertical relaxation time T1 can be reduced.

Known as approaches for the MRA which do not use the contrast medium include a time-of-flight (TOF) method which utilizes a flow-in effect into a slice plane to extract a blood flow image; a phase-sensitive (PS) method which utilizes the presence or absence of phase diffusion by a blood flow to perform differential processing for extracting a blood flow image; a phase-contrast (PC) method which performs differential processing for inverting the polarity of phase diffusion by a blood flow to extract a blood flow image.

These approaches are described in detail in "Magnetic Resonance Imaging; Stark D D et al. edited, The C. V. Mosby Company, pp108–137, 1998"; Keiji Fukui et al., "Research on Cerebral MRA Angio-imaging—First Report—," CT Research, 10(2) 1998, pp133–142; "Magnetic resonance angiography, Dumoulin C L, et al., Radiology 161: 717–720, 1986; "Simultaneous acquisition of Phase-contrast angiograms and stationary-tissue images with Hadamard encoding of flow-induced phase shifts," Dumoulin C L, et al, J. Magnetic Resonance Imaging 1: 399–404, 1991; "Encoding strategies for three-direction Phase-contrast MR imaging," Dumoulin C L, et al., J. Magnetic Resonance Imaging 1: 405–413, 1991; and the like.

On the other hand, an MRA approach using a contrast medium typically combines a T1-reducing contrast medium such as Gd-DTPA and a gradient echo based pulse sequence having a short repetition time TR. This approach repeats excitation in the same region by a high frequency magnetic field at short time intervals of several milliseconds to several tens of milliseconds to saturate spins in portions other than blood flows, and captures high signals from blood flows, in which T1 is reduced due to the contrast medium contained therein, and saturation of spins is hard to occur, to extract a blood flow image.

Further, a DSA approach (Digital Subtraction Angiography) which takes a difference between an image before shadowing and an image after shadowing provides an image which shows blood flows at a higher contrast. Here, in the MRA approach which uses such a contract medium, the contrast medium is typically injected from an elbow vein. The injected contrast medium circulates the heart, arterial system, capillary blood vessels, and vein system in sequence.

Thus, a technology called "dynamic MRA" repeats measurements in each step in the circulation of the contrast medium to produce time-series images of blood flows in respective regions.

The MRA approach and dynamic MRA using such a contrast medium are described in detail in "3D Contrast MR Angiography," 2nd edition, Prince M R, Grist T M and Debatin J F, Springer, pp3–39, 1998, while the dynamic MRA is described in detail in pp16–19 of this literature.

An imaging time for one session in the dynamic MRA as described above is the product of a repetition time TR and the number of phase encoding steps for two-dimensional measurements, and the product of the repetition time TR, the number of phase encoding steps, and the number of slice encoding steps for three-dimensional measurements.

It is therefore desirable to increase the number of phase encoding steps and the number of slice encoding steps for improving the spatial resolution. On the other hand, an increased number of phase encoding steps or slice encoding steps results in a lower temporal resolution. In other words, the spatial resolution and temporal resolution are basically in a trade-off relationship.

To solve such a problem, U.P. Pat. Nos. 5,713,358 and 5,830,143 propose the following measuring methods.

Specifically, these techniques do not measure an overall k-space (space under measurement) in one measurement, but divide the k-space into a plurality of unit regions in a ky-direction, where kx, ky, kz represent three-dimensional directions in the k-space, and control divided regions of the k-space to be measured in each session such that a central region of the k-space (low frequency region) is measured more frequently.

Then, the result of a measurement made in another session is diverted to a region of the k-space which was not measured in a certain session. Alternatively, it is produced through interpolation from the results of a plurality of measurements made in other sessions.

Since the foregoing techniques eliminate the need for executing all phase encoding steps in each session of measurement, they can reduce a measuring time in each session, improve the temporal resolution, and exactly capture a change over time in the central region (low frequency region) of the k-space which relatively determines the contrast important for diagnosis.

DISCLOSURE OF THE INVENTION

However, the techniques described in the aforementioned U.S. Pat. Nos. 5,713,358 and 5,830,143 experience a significantly large degradation in the temporal resolution in a high frequency region.

Also, since the k-space is divided only in a one-dimensional direction, i.e., the ky-direction, the result of measurement depends on the direction, causing a deteriorated quality of an image produced therefrom.

It is an object of the present invention to realize a measuring method and apparatus which are capable of reducing a measuring time in each session, and eliminating the direction dependency from the result of measurement without significantly deteriorating the temporal resolution in a high frequency range when imaging is repeatedly performed in MRI.

In order to attain the aforesaid object, the present invention is configured in the following manner.

(1) In a measuring method in a magnetic resonance imaging apparatus which repeatedly measures an object to be examined by utilizing a nuclear magnetic resonance phenomenon, the method includes:

a region setting step of setting, in a measuring space of the object, an essential measurement region and a divided measurement region including plural divided portions which do not have any region overlapped with the essential measurement region;

a preceding measuring step of combining the essential measurement region with a selected divided portion of the plural divided portions of the divided measurement region to measure a nuclear magnetic resonance signal from the object as data of the measuring space;

a data generating step of combining the essential measurement region with the divided portion having not been selected in the preceding measuring step to measure a nuclear magnetic resonance signal from the object as data of the measuring space; sequentially combining the essential measurement region with the divided portion having not been measured in a preceding measuring step to measure a nuclear magnetic resonance signal from the object;

supplementing the data of the essential measurement region and the data of the divided portion thus measured with the data of the divided portion measured in the preceding measuring step to generate data of the measuring space; and a step of generating an image of the object based on the measuring space generated in the data generating step.

(2) In a measuring method in a magnetic resonance imaging apparatus which repeatedly measures an object to be examined by utilizing a nuclear magnetic resonance phenomenon, the method includes:

a region setting step of setting, in a measuring space of the object, an essential measurement region having a center region of the measuring space and a plurality of peripheral measurement regions which do not have any region overlapped with the essential measurement region;

a preceding measuring step of combining the essential measurement region with a selected peripheral portion of the plurality of the peripheral measurement regions to measure a nuclear magnetic resonance signal from the object as data of the measuring space;

a data generating step of combining the essential measurement region with the peripheral measurement region of the plurality of peripheral measurement regions which has not been selected in the preceding measuring step to measure a nuclear magnetic resonance signal from the object as data of the measuring space; sequentially combining the essential measurement region with the peripheral measurement region having not been measured in a preceding measuring step to measure a nuclear magnetic resonance signal from the object; and supplementing the data of the essential measurement region and the data of the peripheral measurement region thus measured with the data of the peripheral measurement region measured in the preceding measuring step to generate data of the measuring space; and a step of generating an image of the subject based on the measuring space generated in the data generating step.

(3) Preferably, in the aforesaid (2), the measuring space is a three-dimensional space, and a boundary line between the essential measurement region and the respective peripheral measurement regions in the entire three-dimensional measuring space is a line which divides the entire three-dimensional measuring space in at least two dimensional coordinate axis directions of three-dimensional coordinate axes which define the measuring space.

(4) Preferably, in the aforesaid (2) or (3), the measuring space includes a non-measurement region (73, 83, 113) which is not being measured and does not overlap with the essential measurement region and the plurality of peripheral measurement regions.

(5) Preferably, in the aforesaid (2), (3) or (4), the region setting step changes a number of the division of the peripheral measurement region after executing the preceding measuring step and the data generating step for a predetermined number of times.

(6) In a measuring method in a magnetic resonance imaging apparatus which repeatedly measures an object to be examined by utilizing a nuclear magnetic resonance phenomenon, the method includes:

a region setting step of setting, in a measuring space of the object, an essential measurement region having a center region of the measuring space and a peripheral measurement region which does not have any region overlapped with the essential measurement region;

a dividing step of diving a plurality of measuring sampling portions of the peripheral measurement region into a plurality of sampling groups which are distributed almost uniformly in the space;

a preceding measuring step of combining the essential measurement region with a selected sampling group of the plurality of the plurality of sampling groups to measure a nuclear magnetic resonance signal from the object as data of the measuring space;

a data generating step of combining the essential measurement region with the sampling group of the plurality of the sampling groups which has not been selected in the preceding measuring step to measure a nuclear magnetic resonance signal from the object as data of the measuring space; sequentially combining the essential measurement region with the sampling group having not been measured in a preceding measuring step to measure a nuclear magnetic resonance signal from the object; and supplementing the data of the essential measurement region and the data of the sampling group thus measured with the data of the sampling group measured in the preceding measuring step to generate data of the measuring space; and a step of generating an image of the object based on the measuring space generated in the data generating step.

(7) Preferably, in the aforesaid (6), the measuring space is a three-dimensional space, and a boundary line between the essential measurement region and the respective sampling groups in the entire three-dimensional measuring space is a line which divides the entire three-dimensional measuring space into the region and the groups in at least two dimensional coordinate axis directions of three-dimensional coordinate axes which define the measuring space.

(8) Preferably, in the aforesaid (6) or (7), the measuring space includes a non-measurement region (73, 83, 113) which is not being measured and does not overlap with the essential measurement region and the plurality of sampling groups.

(9) Preferably, in the aforesaid (6), (7) or (8), the region setting step changes a divided number of the plurality of sampling groups after executing the preceding measuring step and the data generating step for a predetermined number of times.

(10) A magnetic resonance imaging apparatus which includes a nuclear magnetic resonance generation means for causing an object to be examined nuclear magnetic resonance, an encoding means for phase-encoding a nuclear magnetic resonance signal from the object, and an image reconstruction means for measuring the nuclear magnetic resonance signal and reconstructing an image of the object based on the nuclear magnetic resonance signal thus measured, the magnetic resonance imaging apparatus further includes:

a storage means which stores, as a measuring space of the object, an essential measurement region and a divided measurement region including plural divided portions which do not have any region overlapped with the essential measurement region; and a control means which controls operations of the nuclear magnetic resonance generation means, the encoding means and the image reconstruction means to control measurement of the measuring space determined by phase encoding, and the control means further combines the essential measurement region stored in the storage means with a selected divided portion of the plural divided portions of the divided measurement region to measure a nuclear magnetic resonance signal from the object as data of the measuring space; combines the essential measurement region with the divided portion having not been measured in the preceding measurement to measure a nuclear magnetic resonance signal from the object as data of the measuring space; sequentially combines the essential measurement region with the divided portion having not been measured in a preceding measurement to measure a nuclear magnetic resonance signal from the object; and supplements the data of the essential measurement region and the data of the divided portion thus measured with the data of the divided portion measured in the preceding measurement to generate data of the measuring space and generates data of the measuring space.

(11) Preferably, in the aforesaid (10), the essential measurement region is a center region of the measuring apace, and the divided measurement region is peripheral region of the center region.

(12) Preferably, in the aforesaid (11), the peripheral region is divided into a plurality of sampling groups which are formed by dividing a plurality of measuring sampling portions almost uniformly in space distribution, and the plurality of sampling groups are set as the plurality of divided portions.

According to such a measuring method and apparatus, data measured in each session of measurement necessarily contains a high frequency region component of one divided (peripheral) measurement region. Thus, degree of degradation in the temporal resolution in the high frequency region and also degree of degradation in a generated image is small as compared with the conventional technique disclosed in U.S. Pat. Nos. 5,713,358 and 5,830,143.

Further, according to such a measuring method and apparatus, the measuring space is a three-dimensional space, and a boundary line between the essential measurement region and the respective divided (peripheral) measurement regions in the entire three-dimensional measuring space is a line which divides the entire three-dimensional measuring space in at least two dimensional coordinate axis directions of three-dimensional coordinate axes which define the measuring space. Thus, as compared with U.S. Pat. Nos. 5,713,358 and 5,830,143 in which the measuring space is divided only in the ky-direction, degree of dependency on the direction appearing in the measurement result can be reduced and also the degradation in the quality of a reproduced image can be reduced.

Further, the entire region of the measuring space is not measured but a spatial frequency portion which is not important in the measurement object is set as a non-measurement region, temporal resolution can be improved without largely degrading the matching degree to the measuring object.

Furthermore, when the setting state of a plurality of the peripheral measurement regions is arranged to be changed, even in a case where the degree of importance of the spatial resolution and the temporal resolution changes, the measurement accorded to such a change can be performed.

BRIEF DESCRIPTION OF DRAWINGS

FIG. 5 is a diagram for explaining the measuring method in the first example of the first embodiment of the present invention.

FIG. 10 is a diagram illustrating another example of scanning order in a three-dimensional k-space in the fourth example of the first embodiment of the present invention.

FIG. 11 is a diagram illustrating still another example of scanning order in the three-dimensional k-space in the fourth example of the first embodiment of the present invention.

FIG. 14 is a diagram for explaining a measuring method in a sixth example of the first embodiment of the present invention.

BEST MODE FOR CARRYING OUT THE INVENTION

Figure 1:
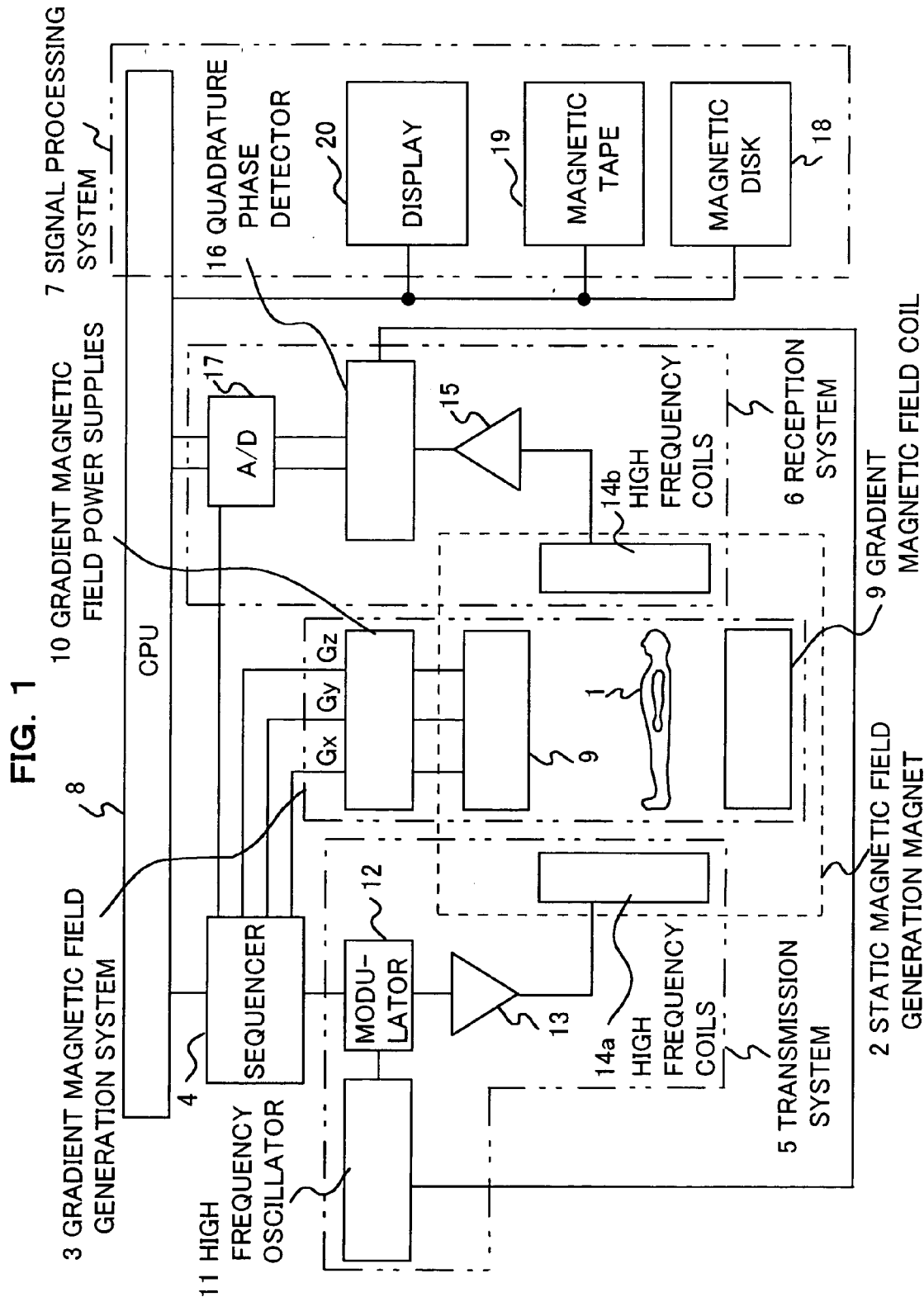
FIG. 1 generally illustrates the configuration of a magnetic resonance imaging apparatus to which the present invention is applied.

FIG. 1 generally illustrates the configuration of an MRI apparatus to which the present invention is applied. In FIG. 1, the MRI apparatus generates a tomographic image of an object to be examined utilizing an NMR phenomenon, and comprises a static magnetic field generating magnet; a gradient magnetic field generation system 3; a sequencer 4; a transmission system 5; a reception system 6; a signal processing system 7; and a central processing unit (CPU) 8.

The static magnetic field generating magnet 2 generates a uniform static magnetic field around an object 1 in its body axis direction or in a direction orthogonal to the body axis. A magnetic field generating means in accordance with a permanent magnet type, a resistive magnetic type, or a superconductive magnet type is disposed in a space having a certain expanse around the object 1.

The gradient magnetic field generation system 3 comprises gradient magnetic field coils 9 wound in the three axial directions X, Y, Z; and gradient magnetic field power supplies 10 for driving the respective gradient magnetic field coils 9. In response to an instruction from the sequencer 4, later described, the gradient magnetic field generation system 3 drives the gradient magnetic field power supplies 10 associated with the respective coils to apply the object 1 with gradient magnetic fields Gx, Gy, Gz in the three axial directions X, Y, Z.

A particular slice or slab of the object 1 can be selectively excited depending on how the gradient magnetic fields are applied, so that the position of a point under measurement (sampling point) and a measuring order can be defined in a measurement space(k-space).

The sequencer 4, which operates under control of a CPU 8, sends a variety of instructions required for collecting data on tomographic images of the object 1 to the gradient magnetic field generation system 3, transmission system 5, and reception system 6.

Operation timings for the gradient magnetic field generation system 3, transmission system 5, and reception system 6 controlled by the sequencer 4 are called a pulse sequence, where a sequence for three-dimensional blood flow imaging is selected as one of pulse sequences. The control of the sequencer 4 will be described later.

The transmission system 5, which irradiates a high frequency magnetic field for promoting nuclear magnetic resonance in nuclei of atoms which make up a vital tissue of the object 1 with a high frequency pulse sent from the sequencer 4, comprises a high frequency oscillator 11, a modulator 12, a high frequency amplifier 13, and a transmission high frequency coil 14a.

The high frequency pulse outputted from the high frequency oscillator 11 is amplitude modulated by the modulator 12 in response to an instruction from the sequencer 4, and the amplitude-modulated high frequency pulse is amplified by the high frequency amplifier 13, and then supplied to the high frequency coil 14a disposed in close proximity to the object 1, thereby irradiating the object 1 with electromagnetic waves.

The reception system 6, which detects an echo signal (NMR signal) emitted by the nuclear magnetic resonance of nuclei of a vital tissue in the object 1, comprises a reception high frequency coil 14a, an amplifier 15, a quadrature phase detector 16, and an A/D converter 17. Electromagnetic waves (NMR signal) from the object 1 responsive to the electromagnetic waves irradiated from the transmission high frequency coil 14a are detected by the high frequency coil 14b disposed in close proximity to the object 1.

The detected echo signal is inputted to the A/D converter 17 through the amplifier 15 to convert to a digital amount, further sampled digital signal is inputted to the quadrature phase detector 16 at a timing determined by an instruction from the sequencer 4 to produce two sequences of collected data which are sent to the signal processing system 7.

The signal processing system 7 comprises the CPU 8, a recording device such as a magnetic disk 18, a magnetic tape 19, and the like, and a display 20 such as a CRT. The CPU 8 performs processing such as three-dimensional Fourier transform, calculation of correction coefficients, reconstruction of images, and the like. A signal intensity distribution on an arbitrary cross section or a distribution derived from proper processing performed on a plurality of signals is transformed into an image which is displayed on the display 20 as a tomographic image.

In FIG. 1, the transmission and reception high frequency coils 14a, 14b and the gradient magnetic field coil 9 are disposed within a magnetic field space of the static magnetic field generating magnet 2 placed in a space around the object 1.

Next, a dynamic MRA imaging operation will be described in the MRI apparatus.

First described is a pulse sequence used in the measurement.

The sequencer 4 controls operation timings for the gradient magnetic field generation system 3, transmission system 5, and reception system 6 in accordance with a predetermined pulse sequence, here, a three-dimensional MRA sequence. This pulse sequence has been previously incorporated in a memory associated with the CPU 8 as a program, and can be executed through an appropriate selection made by the user in accordance with the purpose of imaging, as is the case with other pulse sequences. Specifically, upon selection of MRA using a contrast medium through an input device of the CPU 8, the sequencer 4 is controlled by the CPU 8 to execute the three-dimensional MRA sequence.

Figure 2:
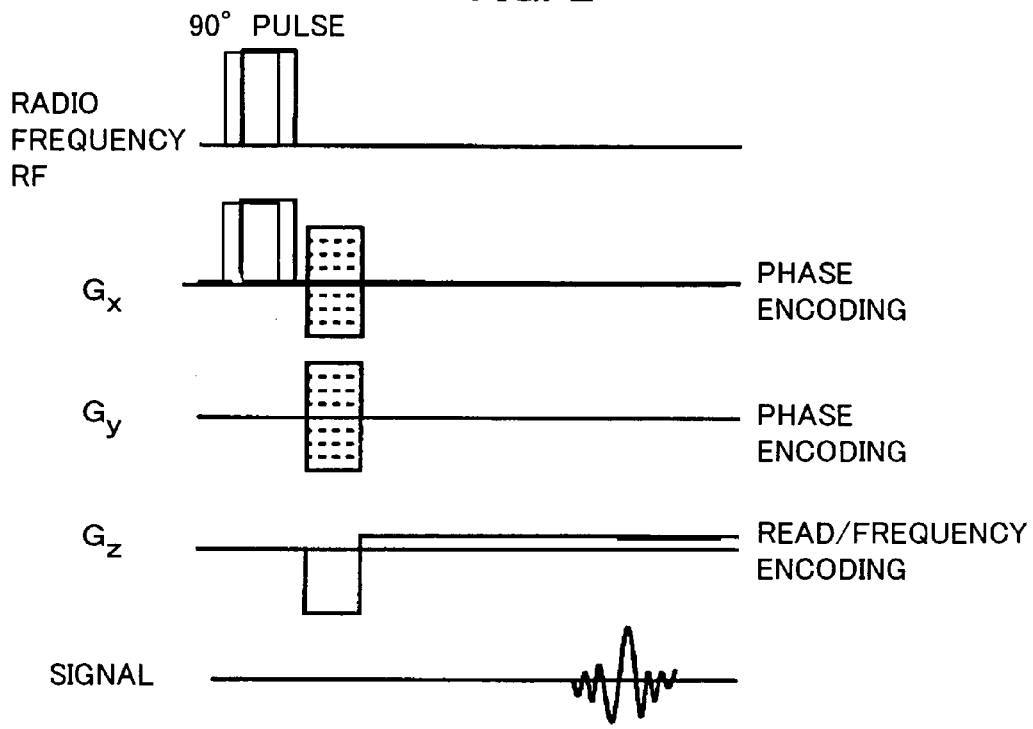
FIG. 2 is a timing chart illustrating an example of a pulse sequence in the measurement of the magnetic resonance imaging apparatus to which the present invention is applied.

This pulse sequence is a sequence based on a gradient echo method, for example, as illustrated in FIG. 2, which is a general three-dimensional sequence. In some cases, however, a flow compensation such as Gradient Moment Nulling and the like may be added.

In the illustrated example, after a region (slab) including a target blood vessel is applied with a high frequency magnetic field pulse RF for excitation, the region is applied with a phase encode gradient magnetic field Gz in the Z-direction and a phase encode gradient magnetic field Gy in the Y-direction, and then applied with a read out/frequency encode gradient magnetic field Gx. Meanwhile, its polarity is inverted to measure an echo signal.

In the three-dimensional imaging, such a pulse sequence is repeated at intervals of a predetermined repetition time TR, while changing a combination of magnetic field strengths of the phase encode gradient magnetic field Gz in the Z-direction and the phase encode gradient magnetic field Gy in the Y-direction, to capture three-dimensional data.

Here, the numbers of encoding steps in the Z- and Y-directions determine the numbers into which the region is divided in the Z- and Y-directions, and set, for example, to 128, 256, or the like. Also, the numbers of encoding steps in the Z- and Y-directions define the size of a ky-kz plane in the k-space.

Specifically, in the sequence of FIG. 2, a signal measured when a certain value of the gradient magnetic field strength Gz is combined with a certain value of the gradient magnetic field strength Gy is placed at coordinates (ky, kz) in the k-space corresponding to the values of Gz, Gy. Conversely speaking, sampling certain coordinates (ky1, kz1) on the ky-kz plane in the k-space means the execution of the pulse sequence of FIG. 2 in combination of the gradient magnetic field Gy corresponding to ky1 with the gradient magnetic field Gz corresponding to kz1. On the other hand, not sampling the coordinates (ky1, kz1) means the omission of the execution of the pulse sequence of FIG. 2 in the combination of the gradient magnetic field Gy corresponding to ky1 with the gradient magnetic field Gz corresponding to kz1.

The basic dynamic MRA in the prior art fixes the numbers of encoding steps and step widths in the Z- and Y-directions in each session of measurement, and executes the pulse sequence of FIG. 2 for all combinations of the gradient magnetic fields Gy and Gz in each session of measurement to produce the three-dimensional k-space filled with data at all coordinates.

In contrast, a first embodiment of the present invention does not fix the numbers of steps and step widths in the Z- and Y-directions in each session of measurement in the dynamic MRA imaging, and controls each session of measurement in the following manner.

Specifically, in the first embodiment of the present invention, an essential measurement region which is a central region, and a plurality of peripheral measurement regions (divided measurement regions) around the essential measurement region are set on a two-dimensional k-space which has coordinate axes ky, kz, the magnitudes of which have been previously determined in accordance with the numbers of possible phase encoding steps in the Z- and Y-directions.

Here, each of the peripheral measurement regions may partially include the same region as other peripheral measurement regions. The essential measurement region is measured without fail in each session of measurement, while the respective peripheral measurement regions are measured one by one in a desired order in each session of measurement, for example, in a circular manner.

For a region in the k-space which was not measured in each session of measurement, data is acquired through a diversion from the result of measurement in the most recent past session of measurement in which portions of the k-space not measured in that session had been measured and which is prior to that session. Then, as described above, in each session of measurement, a three-dimensional Fourier transform is performed on the k-space filled with data in the essential measurement region and all the peripheral measurement regions by the measurement in that session and the diversion from the result of measurements in the past session, to produce three-dimensional data which is projected to provide a two-dimensional image.

Alternatively, a difference may be taken between the reconstructed three-dimensional data and three-dimensional data previously measured before injection of the contrast medium, and be used as final three-dimensional data. While this difference is preferably a complex difference, it may be a difference between absolute magnitude values. Alternatively, the reconstruction may be performed after taking a complex difference between k-space data after data is filled in all the regions in each session and the k-space data previously measured before the injection of the contrast medium.

Further, the three-dimensional data is placed in a virtual two-dimensional screen as well as in a virtual three-dimensional coordinate system in a predetermined or a specified placement relationship, and the three-dimensional data is projected onto the virtual two-dimensional screen to generate a two-dimensional image which is displayed.

Figure 3:
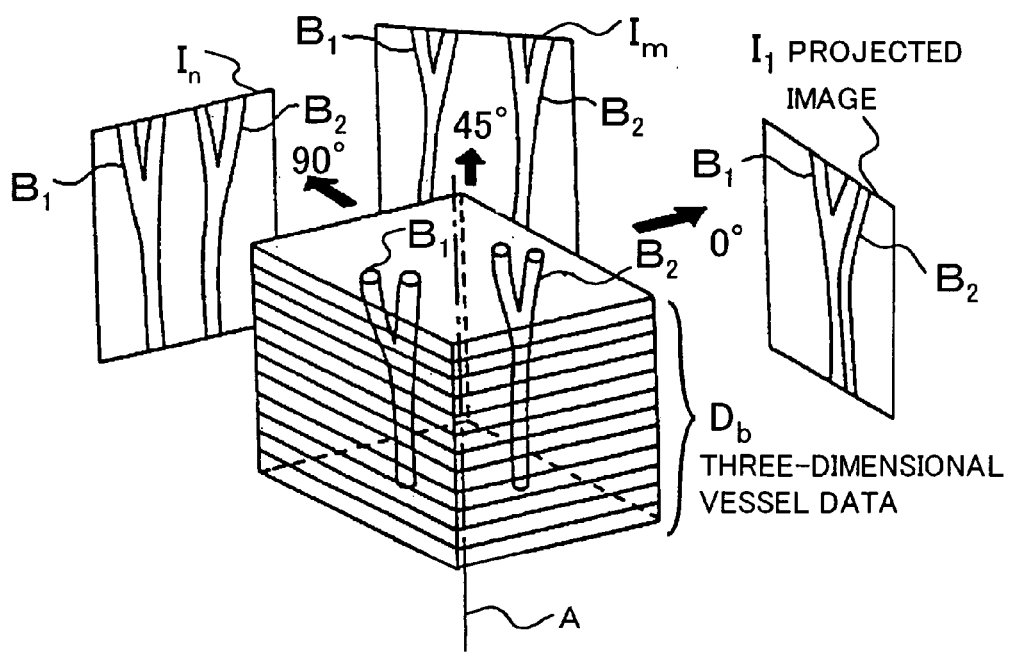
FIG. 3 is a diagram illustrating an example for generating a two-dimensional image by projecting a three-dimensional data in the present invention.

Here, while the three-dimensional data may be projected in an arbitrary direction, it is generally projected in a direction of a coronal section, a sagittal section, or axial traverse. Further, two-dimensional images may be sequentially generated while the projecting direction is rotated about a certain axis, and they may be connected to generate a moving image. For example, as illustrated in FIG. 3, three-dimensional blood vessel data Db may be rotated over 45 degrees each time about an A-axis and projected to generate three two-dimensional images Ix (Il, Im, In) which may be connected to generate a moving image.

The generation of the two-dimensional images is implemented by a known rendering approach such as surface rendering, volume rendering, and the like, other than a combination of a maximum intensity projection which projects a maximum of voxels existing at a position projected onto certain coordinates on the two-dimensional screen to those coordinates, and a ray tracing.

Next, in the first embodiment of the present invention as described above, description will be made on specific examples of the setting of the peripheral measurement regions and measurements of the essential measurement region and peripheral measurement regions.

To begin with, a first example will be described.

Figure 4A:
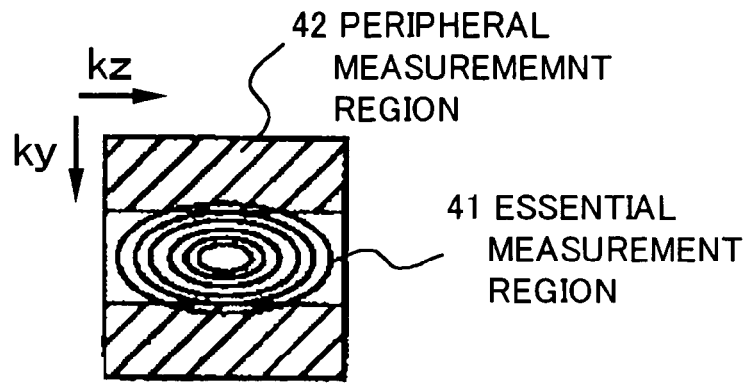
FIGS. 4A and 4B are diagrams for explaining a measuring method in a first example of the first embodiment of the present invention.

In this first example, as illustrated in FIG. 4A, a three-dimensional k-space is divided into three in the ky-direction, and an upper and a lower region (shaded regions) in FIG. 4A are designated the peripheral measurement regions 42, while a central region is designated the essential measurement region 41. Then, as illustrated in FIG. 4B, the essential measurement region 41 is measured without fail in each session of measurement, while each of the peripheral measurement regions is alternately measured one by one in each session of measurement.

For a region in the three-dimensional k-space which was not measured in each session of measurement, data is acquired through a diversion from the result of measurement in the session which is the closest past session in which the region in the three-dimensional k-space, which was not measured in that session, had been measured.

For the reconstruction of an image, in each session of measurement, a three-dimensional Fourier transform is performed on the three-dimensional k-space filled with data in the session of measurement and the diverted result of measurement in a past session, as described above, to produce three-dimensional data which is projected to provide a two-dimensional image.

Figure 4B:
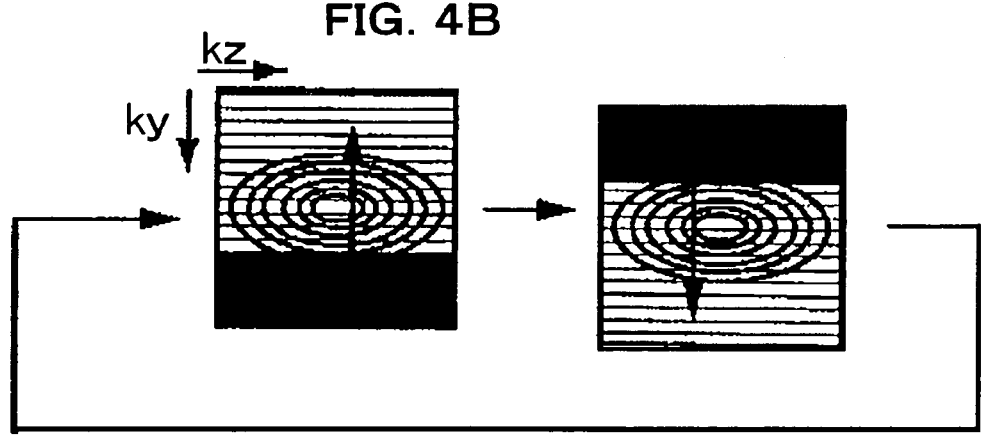

In FIG. 4B, a solid black region represents a region which is not measured in a concerned session of measurement. The same applies to the following drawings.

Figure 6:
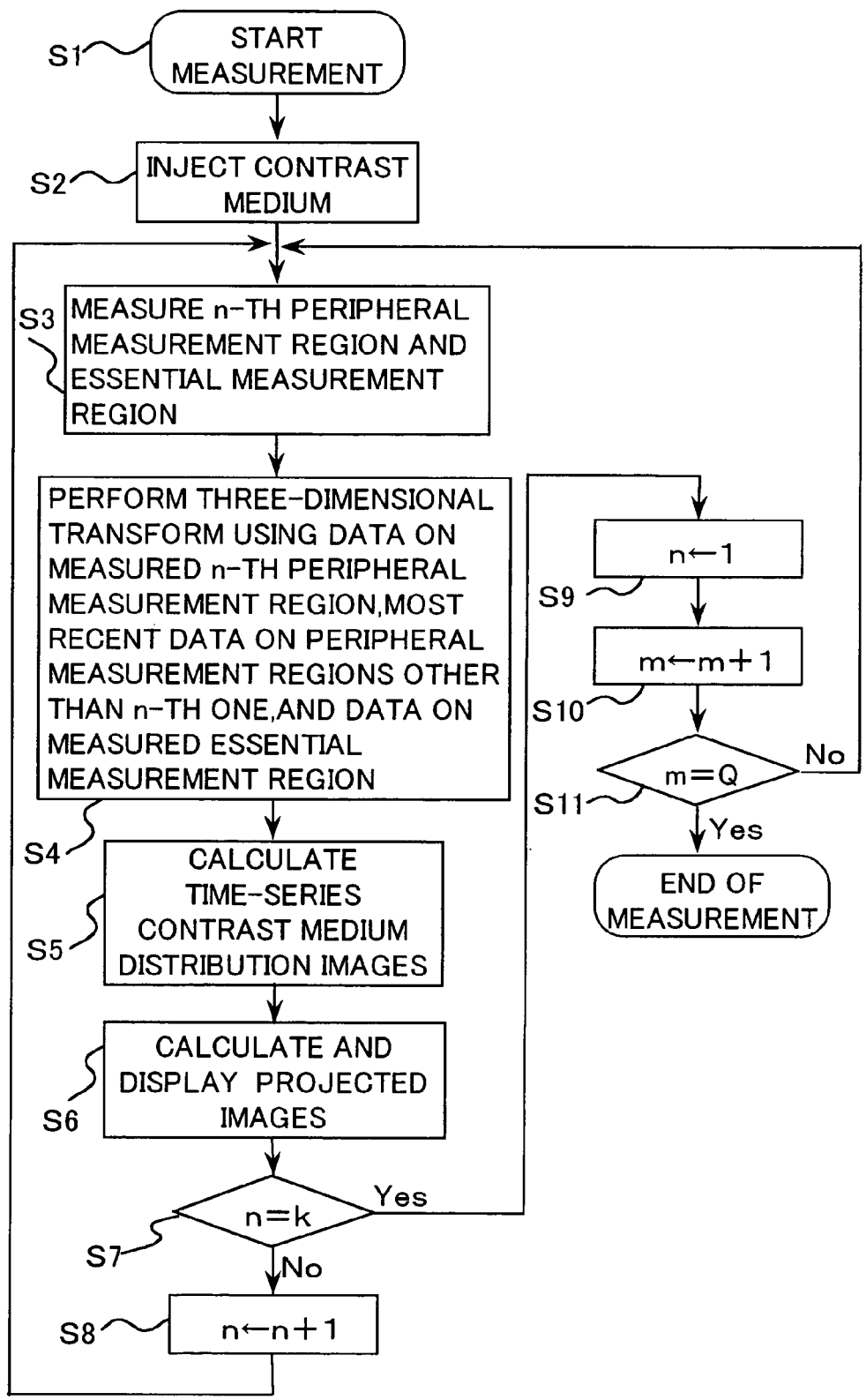
FIG. 6 is a flowchart for explaining the operation of the measuring method in the first example of the first embodiment of the present invention.

FIG. 5 is a diagram for describing an example of a first exemplary measurement procedure in the first embodiment of the present invention, and FIG. 6 is an operational flow chart.

Specifically, in FIGS. 5 and 6, a measurement is started at step S1, and a contrast medium is injected into a vein at step S2 (a in FIG. 5). Next, as illustrated in step S3 and b, c in FIG. 5, the essential measurement region in the three-dimensional k-space is measured without fail, and an n-th peripheral measurement region in the three-dimensional k-space is measured in each session of measurement. n is initially set to one.

At step S4 and d in FIG. 5, the three-dimensional k-space is filled with the data on the essential measurement region measured in that session, the data on the n-th peripheral measurement region measured in that session, and the most recent data on the peripheral measurement regions other than the n-th one, and a three-dimensional Fourier transform is performed on the k-space filled with the data. In the illustrated example, since no preceding measured data is available in the first session of measurement, the three-dimensional k-space may be filled with data before measurement.

Subsequently, as illustrated in step S5 and d in FIG. 5, three-dimensional image data (time-series contrast medium distribution images) is calculated.

Then, as illustrated in step S6 and e in FIG. 5, the three-dimensional image data is projected to produce a two-dimensional image (projected blood vessel image) which is displayed on a display screen or the like.

Then, the flow proceeds to step S7, where it is determined whether or not n is equal to k. This k is the number of divided peripheral measurement regions, and is two in this example. If n is not equal to k, the flow proceeds to step S8, where n+1 is set to n, followed by the flow returning to step S3. Subsequently, the aforementioned steps S3 to S6 are executed. In this way, the next peripheral measurement region and the essential measurement region are measured.

Conversely, if n is equal to k at step S7, the flow proceeds to step S9, where n is reset to one, and m+1 is set to m at step S10. m is provided for counting the number of times of measurements, and is initially set to one.

Next, it is determined at step S11 whether or not m is equal to Q. The flow returns to step S3 if not equal, while the measurement is terminated if m is equal to Q. This Q is set to the number of times at which the measurement is terminated.

As a result of the foregoing operation, each blood vessel is sequentially displayed at a high contrast as the contrast medium flows into a blood vessel A, a blood vessel B, a blood vessel C, as illustrated in FIG. 5.

In the first example, the direction in which the three-dimensional k-space is scanned for measurement in each session of measurement, i.e., the order of the phase encoding in the Z- and Y-directions is such that the essential measurement region 41 is scanned from the side near a peripheral measurement region 42 which is not measured in that session, toward the peripheral measurement region 42 which is measured in that session, as indicated by an arrow in the k-space in FIG. 4B. However, the direction is not limited to this.

According to the first example in the first embodiment of the present invention described above, since a measurement in each session includes without fail components in a high frequency region of one peripheral measurement region out of the plurality of divided peripheral measurement regions, the temporal resolution is deteriorated less in the high frequency region, as compared with the prior art which measures the high frequency region at a low frequency (for example, the techniques described in U.S. Pat. Nos. 5,713, 358 and 5,830,143). Consequently, a generated image also suffers from a less deterioration in quality.

Next, description will be made on a second example in the first embodiment of the present invention.

Figure 7A:
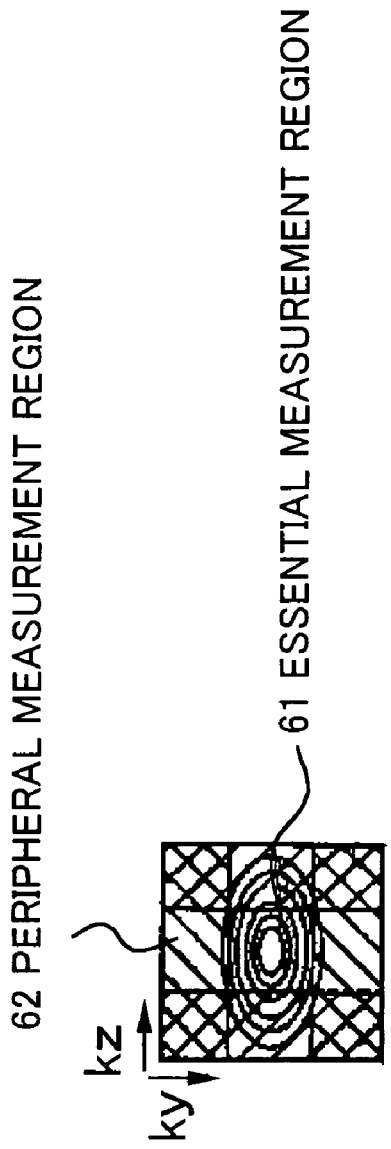
FIGS. 7A and 7B are diagrams for explaining a measuring method in a second example of the first embodiment of the present invention.

In this second example, as illustrated in FIG. 7A, the three-dimensional k-space is divided into three in the ky-direction, wherein an upper and a lower region in FIG. 7A are designated peripheral measurement regions 62, and the three-dimensional k-space is divided into three in the kz-direction, where a left and a right region in FIG. 7A are designated peripheral measurement regions 63. A central region surrounded by these four peripheral measurement regions 62 (upper and lower), 63 (left and right) is designated an essential measurement region 61.

Figure 7B:
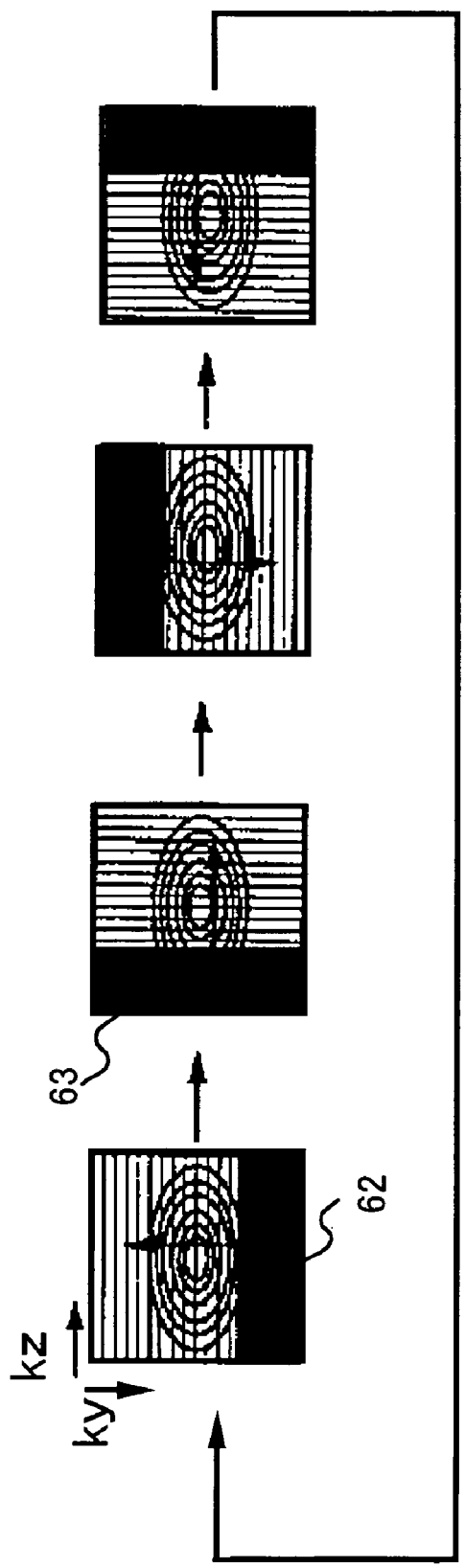

As illustrated in FIG. 7B, the essential measurement region 61 is measured without fail in each session of measurement, while the respective peripheral measurement regions 62, 63 are measured one by one in a desired order in each session of measurement. The order in which the peripheral measurement regions 62, 63 are measured may be circular, for example, as illustrated in FIG. 7B. Alternatively, the upper and lower (or left and right) peripheral measurement regions 62 (63) may be measured in sequence, followed by sequential measurements of the left and right (upper and lower) peripheral measurement regions 63 (62).

Similar to the aforementioned first example, for regions in the three-dimensional k-space which was not measured in each session of measurement, data is acquired through a diversion from the result of measurement in the session which is the closest past session in which the regions in the three-dimensional k-space, which were not measured in that session, had been measured. In each session of measurement, a three-dimensional Fourier transform is performed on the three-dimensional k-space filled with data in the session of measurement and the diverted result of measurement in a past session to produce three-dimensional data which is projected to provide a two-dimensional image.

In other words, the operational flow in the second example is similar to the operational flow illustrated in FIG. 6. However, in the second example, the value of k is four.

Likewise, in the second example, the direction in which the three-dimensional k-space is scanned for measurement in each session of measurement, i.e., the order of the phase encoding in the Z- and Y-directions may be such that the essential measurement region is scanned from the side near a peripheral measurement region which is not measured in that session, toward the peripheral measurement region which is measured in that session, as illustrated. However, the direction is not limited to this.

As described above, according to the second example in the first embodiment of the present invention, since two boundaries are set between the essential measurement region and the peripheral measurement regions in the ky- and kz-directions, the direction dependency, found in the result of measurement, is reduced as compared with the prior art which divides the k-space only in the ky-direction (for example, the techniques described in U.S. Pat. Nos. 5,713, 358 and 5,830,143), thereby making it possible to alleviate a deterioration in the quality of a generated image.

Figure 8A:
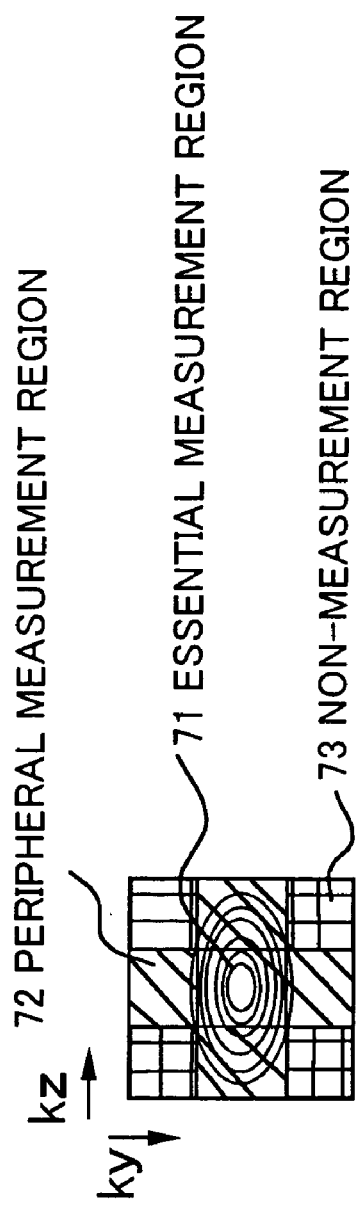
FIGS. 8A and 8B are diagrams for explaining a measuring method in a third example of the first embodiment of the present invention.
Figure 8B:
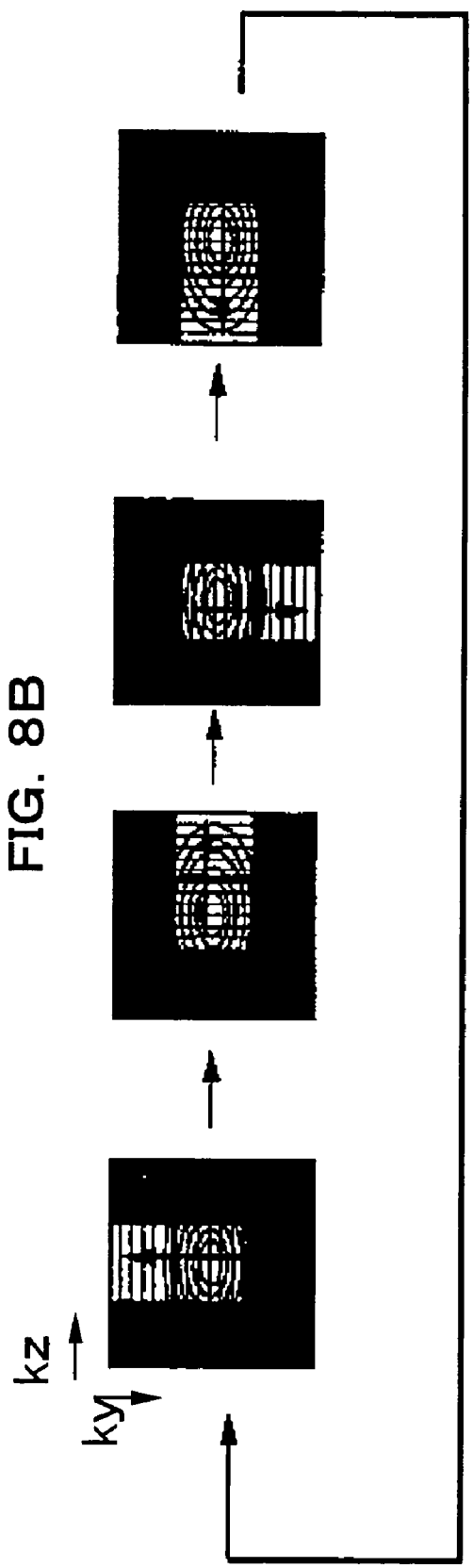

FIGS. 8A and 8B are diagrams for explaining a third example in the first embodiment of the present invention. In this third example, as illustrated in FIG. 8A, the three-dimensional k-space is divided into three in the ky-direction and the three-dimensional k-space is divided into three in the kz-direction thereby to obtain nine regions. In these nine regions, four regions, that is, the center region along the kz-direction on the upper side, the center region along the kz-direction on the lower side, the center region along the ky-direction on the left side and the center region along the ky-direction on the right side are designated peripheral measurement regions 72. The center region surrounded by the peripheral measurement regions 72 is designated an essential measurement region 71. The remaining regions are designated non-measurement regions 73 where measurement is not performed.

In the third example, also as illustrated in FIG. 8B, the essential measurement region 71 is measured without fail in each session of measurement, while the respective peripheral measurement regions 72 are measured one by one in a desired order in each session of measurement For regions in the three-dimensional k-space which was not measured in each session of measurement, data is acquired through a diversion from the result of measurement in the session which is the closest past session in which the regions in the three-dimensional k-space, which were not measured in that session, had been measured. In each session of measurement, three-dimensional k-space data is obtained in which the regions other than the non-measurement regions are filled through a diversion from the result of measurement in the present session and the past session.

Then, after zero-filling is performed on the non-measurement regions, a three-dimensional Fourier transform is performed on the k-space data to produce three-dimensional image data which is then projected to provide a two-dimensional image.

Likewise, in the third example, the direction in which the three-dimensional k-space is scanned for measurement in each session of measurement, i.e., the order of the phase encoding in the Z- and Y-directions may be such that the essential measurement region is scanned from the side opposite to a peripheral measurement region which is not measured in that session, toward the peripheral measurement region which is measured in that session, as illustrated. However, the direction is not limited to this.

According to the third example in the first embodiment of the present invention described above, the technical effects similar to that of the first and second examples can be obtained. Further, since the corner regions on the three-dimensional k-space which are relatively not so important for diagnosis etc. are designated the non-measurement regions, the measurement can be repeated in a shorter time, whereby the temporal resolution can be improved whilst a generated image suffers from a relatively small deterioration in quality.

Next, description will be made on a fourth example in the first embodiment of the present invention.

Figure 9A:
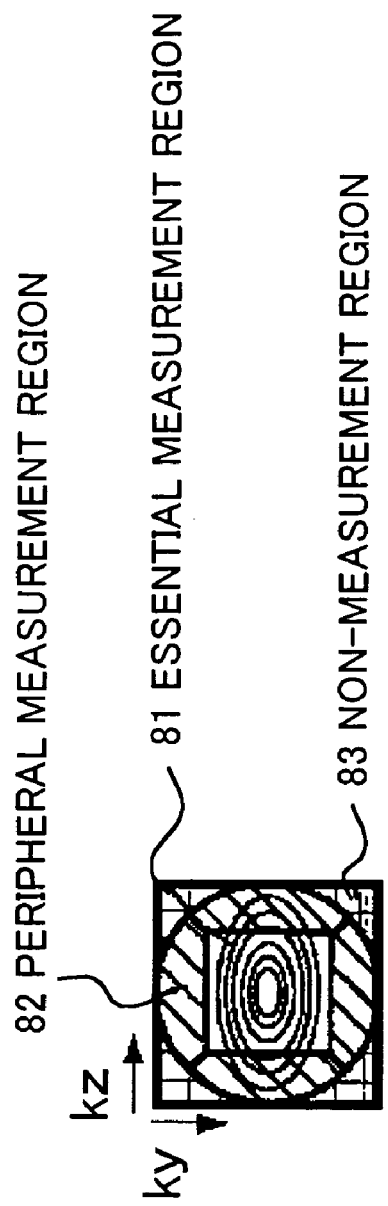
FIGS. 9A and 9B are diagrams for explaining a measuring method in a fourth example of the first embodiment of the present invention.

In this fourth example, as illustrated in FIG. 9A, the three-dimensional k-space is divided into a region within an inscribed circle inscribing to the ky-kz plane and regions outside of the inscribed circle, wherein the outside regions are designated non-measurement regions 83. Further, the region within the inscribed circle is divided into a region within a quadrangle contained within the circle and a region outside of the quadrangle, wherein the region within the quadrangle is designated an essential measurement region 81.

A region between the regions 83 and the region 81, that is, the region which is the inside of the circle and the outside of the region 81 is equally divided into four regions, wherein these four regions are designated regions 82.

Incidentally, when the ky-kz plane is a square, the circle becomes complete round, whilst when the ky-axis and the kz-axis differ in their lengths and so the ky-kz plane is a rectangle, the circle becomes elliptical. In the present specification, the "circle" is defined to include such an ellipse.

Figure 9B:
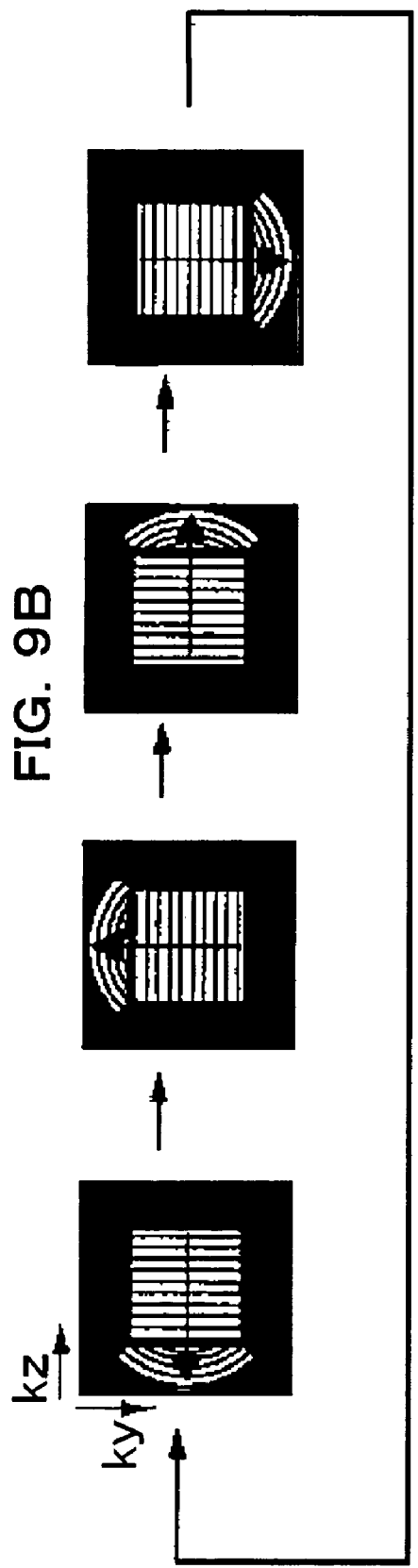

In the fourth example, also as illustrated in FIG. 9B, the essential measurement region 81 is measured without fail in each session of measurement, while the respective peripheral measurement regions 82 are measured one by one in a desired order in each session of measurement For regions in the three-dimensional k-space which was not measured in each session of measurement, like the first example, data is acquired through a diversion from the result of measurement in the session which is the closest past session in which the regions in the three-dimensional k-space, which were not measured in that session, had been measured. In each session of measurement, three-dimensional k-space data is obtained in which the regions other than the non-measurement regions are filled through a diversion from the result of measurement in the present session and the past session.

In this example, zero-filling may also be performed on the non-measurement regions. A three-dimensional Fourier transform is performed on the k-space data to produce three-dimensional image data which is then projected to provide a two-dimensional image.

The fourth example can attain the similar effect as that of the third example.

Likewise, in the fourth example, the direction in which the three-dimensional k-space is scanned for measurement in each session of measurement, i.e., the order of the phase encoding in the Z- and Y-directions may be such that the essential measurement region is scanned from the side opposite to a peripheral measurement region which is not measured in that session, toward the peripheral measurement region which is measured in that session, as illustrated. However, the direction is not limited to this.

The scanning may be performed spirally as illustrated in FIG. 10 instead of the raster scanning described above. In this case, the scanning is started from a portion closest to the origin of the ky-kz plane. Alternatively, the scanning may be performed spirally in another manner as illustrated in FIG. 11 that, of the essential measurement region, the scanning is started from a portion most away from the origin until the scanning point reaches the origin of the ky-kz plane and the scanning is started from a portion closest to the origin of the ky-kz plane after the scanning point reaches the origin, and then the peripheral measurement regions are scanned.

Next, description will be made on a fifth example in the first embodiment of the present invention.

Figure 12A:
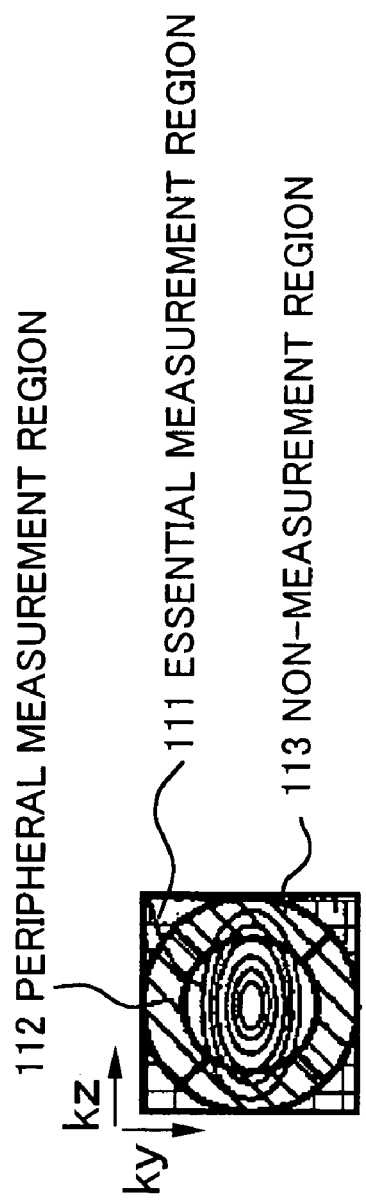
FIGS. 12A and 12B are diagrams for explaining a measuring method in a fifth example of the first embodiment of the present invention.

In this fifth example, as illustrated in FIG. 12A, the region within a first circle set on the ky-kz plane is designated an essential measurement region 111. Further, a second circle larger than the first circle is set on the ky-kz plane so as to contain at least the essential measurement region therein. The region within the second circle and the outside of the first circle is equally divided into four regions along the peripheral direction of the circles and these four regions are designated peripheral measurement regions 112.

The region outside of the peripheral measurement regions 112, that is, the region outside of the second circle is a non-measurement region 113.

Figure 12B:
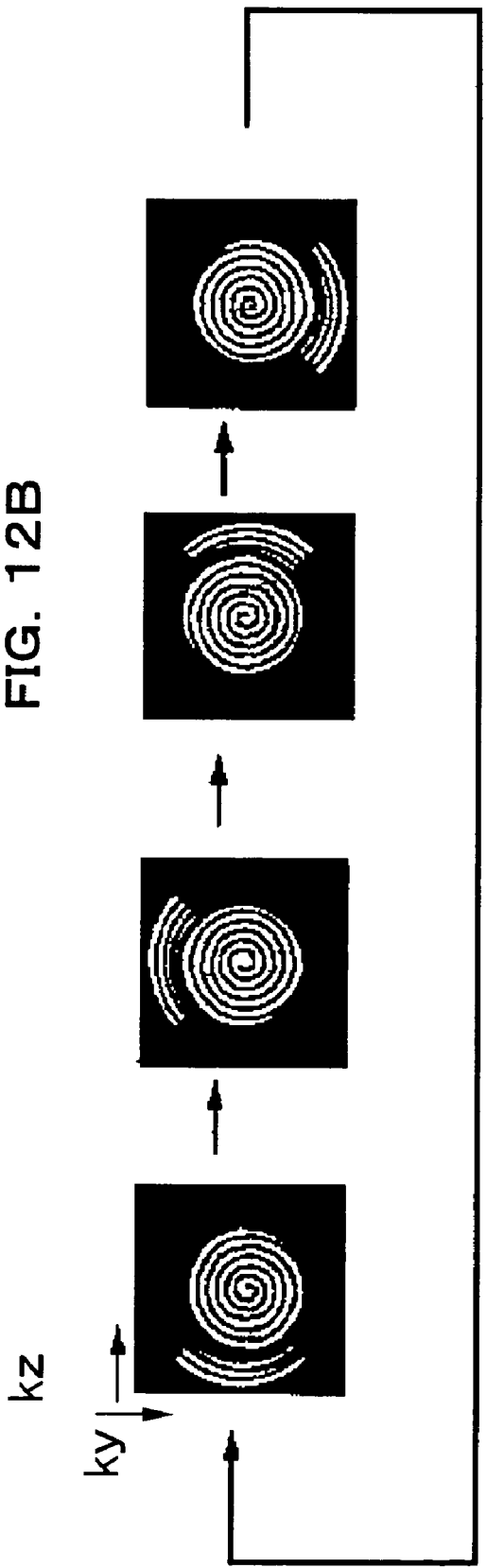

Then, as illustrated in FIG. 12B, the essential measurement region 111 is measured without fail in each session of measurement, while the respective peripheral measurement regions 112 are measured one by one in a desired order in each session of measurement.

In this fifth example, like the first example, for regions in the three-dimensional k-space which was not measured in each session of measurement, data is acquired through a diversion from the result of measurement in the session which is the closest past session in which the regions in the three-dimensional k-space, which were not measured in that session, had been measured. In each session of measurement, three-dimensional k-space data is obtained in which the regions other than the non-measurement regions are filled by the measurement data through a diversion from the result of measurement in the present session and the past session. In this example, zero-filling is also performed on the non-measurement regions 113. A three-dimensional Fourier transform is performed on the k-space data to produce three-dimensional image data which is then projected to provide a two-dimensional image.

The fifth example can attain the similar effect as that of the third example.

Figure 13:
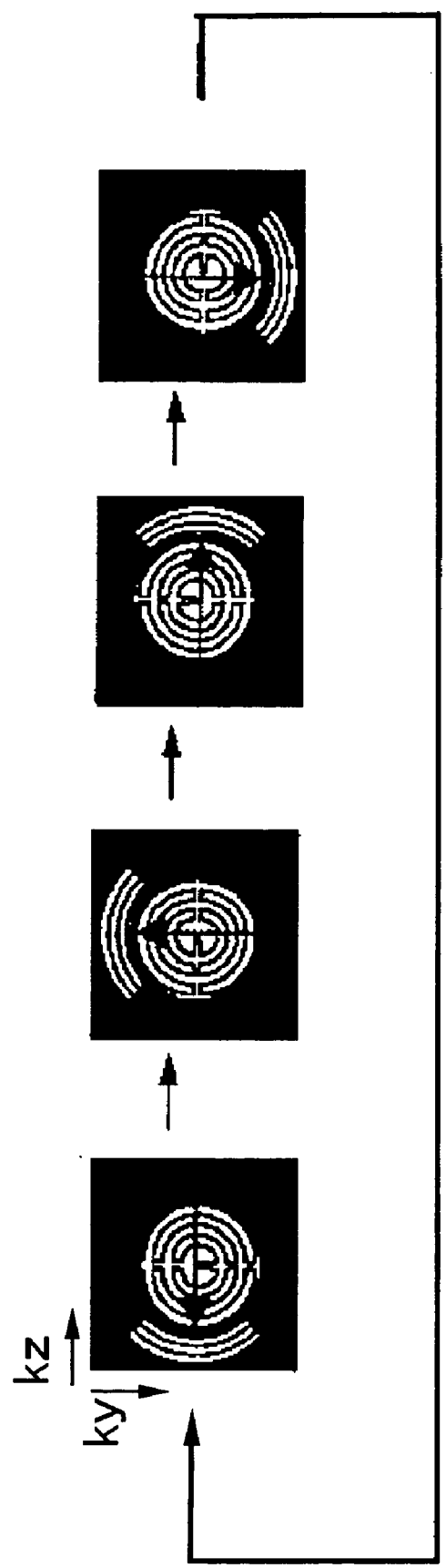
FIG. 13 is a diagram illustrating another example of scanning order in the three-dimensional k-space in the fifth example of the first embodiment of the present invention.

Likewise, in the fifth example, the direction in which the three-dimensional k-space is scanned for measurement in each session of measurement, i.e., the order of the phase encoding in the Z- and Y-directions may be arbitrary. That is, as shown in FIG. 12B, the scanning may be performed spirally in a manner that the scanning is started from a portion closest to the origin of the ky-kz plane (the center portion of the first circle) and then the scanning point goes away from the origin gradually. Alternatively, the scanning maybe performed spirally in another manner as illustrated in FIG. 13 that, of the essential measurement region, a semicircle away from the origin is scanned until the scanning point reaches the origin of the ky-kz plane, then a semicircle away from the origin is scanned, whereby a semicircle is scanned sequentially and so the scanning point approaches to the origin of the circle gradually. After the scanning point reaches the origin of the circle, of the other semicircle, the scanning is started from a portion closest to the origin of the ky-kz plane, then after the semicircle away from the origin has been scanned, the peripheral measurement regions are scanned.

Next, description will be made on a sixth example in the first embodiment of the present invention.

In this sixth example, as illustrated in FIG. 14, the magnitude (the number of division) of a peripheral measurement region 132 is changed in the flow of a series of measurement procedure.

That is, during a period where a higher temporal resolution is required, the number of the division of the peripheral measurement region is made large thereby to make small the peripheral measurement region measured in each session of measurement, whereby the measurement can be repeated in a shorter time period.

In contrast, during a period where a higher spatial resolution is required, the number of the division of the peripheral measurement region is made small thereby to make large the peripheral measurement region measured in each session of measurement, whereby the measurement can be repeated with a high spatial resolution.

In other words, as illustrated in a of FIG. 14, the number of the division of the peripheral measurement region is made eight, for example, before and after the injection of contrast medium and during a time period T1 where the contrast medium reaches major aorta, whereby each of the peripheral measurement regions 132 is set to be small so that the measurement can be made with a high temporal resolution.

Further, as illustrated in a of FIG. 14, at a time point where the contrast medium passes through an arterial phase and reaches a venous phase, the number of the division of the peripheral measurement region is made small thereby to make large the region to be measured, whereby the measurement can be made according to the change of the blood flow state. For example, the number of the division is made 4 at a time period T2 and made 2 at a time period T3.

The sixth example can attain the similar effect as that of the third example. Further, since the sixth example is configured to change the number of the division of the peripheral measurement region in accordance with the time period during which the temporal resolution is required and the time period during which the spatial resolution is required, an image data with a high resolution according to need can be attained.

According to the sixth example illustrated in FIG. 14, a region within a circle set on the ky-kz plane is designated an essential measurement region 131, n regions obtained by dividing in the peripheral direction equally a region between the essential measurement region 131 and a circle set so as to contain the essential measurement region 131 are designated peripheral measurement regions 132, and the number of n is changed in accordance with an elapsed time from the start of the measurement thereby to change the size of the respective peripheral measurement region.

The method of changing the size of the peripheral measurement region is not limited thereto, and the method may be realized by suitably combining the setting method of the peripheral measurement regions illustrated in FIG. 4A and the setting methods of the peripheral measurement regions illustrated in FIG. 7A or 8A.

Although the operation flow of the sixth example is similar to the operation flow illustrated in FIG. 6, the six example is arranged to change a value k in accordance with an elapsed time of measurement.

Next, description will be made on the second embodiment of the present invention.

According to the second embodiment, on the ky-kz plane of the three-dimensional k-space having kx, ky and kz coordinate axes which sizes are determined according to the numbers of frequency encoding in the x-direction and the numbers of encoding steps in the Z- and Y-directions, an essential measurement region is set as a center region centered around the origin and a peripheral measurement region is set around the essential measurement region. For the peripheral measurement region, all the sampling points existing within the peripheral measurement region are divided into plural groups.

Although this is the same as the first embodiment, the second embodiment differs from the first embodiment in a manner that the peripheral measurement region is divided not into plural regions but into plural groups such that the sampling points in each of the groups are distributed so as not to be clustered spatially from one another and the respective groups have almost same sampling points.

Such dividing setting information of the sampling points is stored in a memory of the CPU 8 together with the sequence of the measurement described later.

In this embodiment, the essential measurement region is measured without fail in each session of measurement, while the respective groups of the peripheral measurement region are measured one by one in a desired order in each session of measurement. Thus, at a time point where the measurements performed for the number of times equal to the number of the groups having been divided, data of all the sampling points of the peripheral measurement region can be obtained.

FIGS. 15A, 15B, 15C and 16 show a first example of the second embodiment where the peripheral measurement region is divided into three groups. In this case, the explanation will be made as to a ky-kz space having a matrix size of 5×9 in order to simplify the explanation.

Figure 15A:
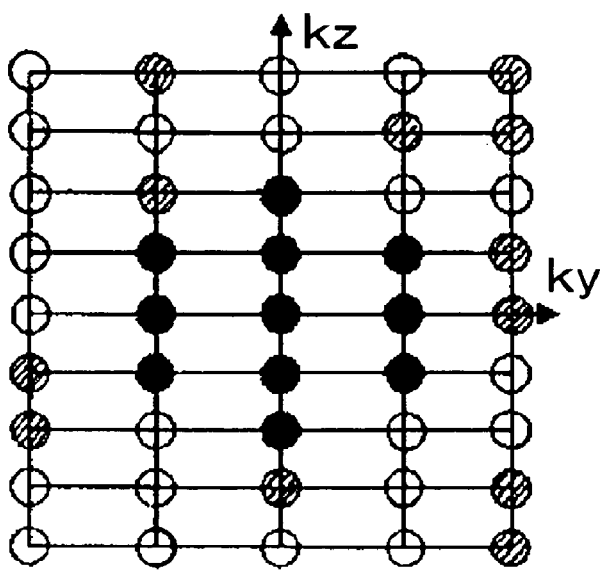
FIGS. 15A, 15B and 15C are diagrams for explaining a measuring method in a first example of the second embodiment of the present invention.
Figure 15B:
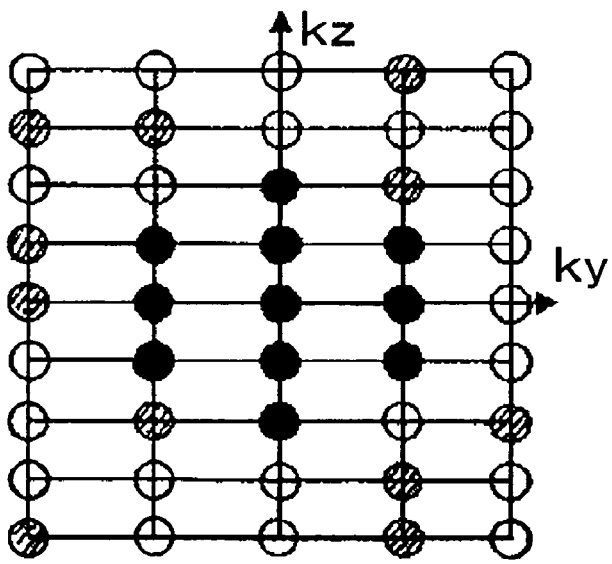
Figure 15C:
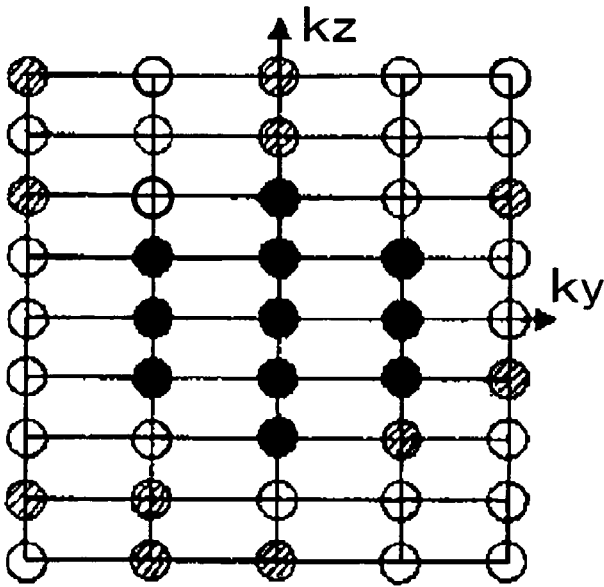

In this first example, as illustrated in FIGS. 15A, 15B and 15C, eleven sampling points including the origin of the coordinates illustrated by black circles are designated the essential measurement region, while the remaining region excluding the essential measurement region are designated the peripheral measurement region.

Thirty-four sampling points of the peripheral measurement region are divided into three groups having different sampling points as shown by hatched circles such that the numbers of the sampling points of FIGS. 15A, 15B and 15C are 12, 11 and 11, respectively. In each of these three groups, the sampling points are almost uniformly dispersed spatially.

Figure 16:
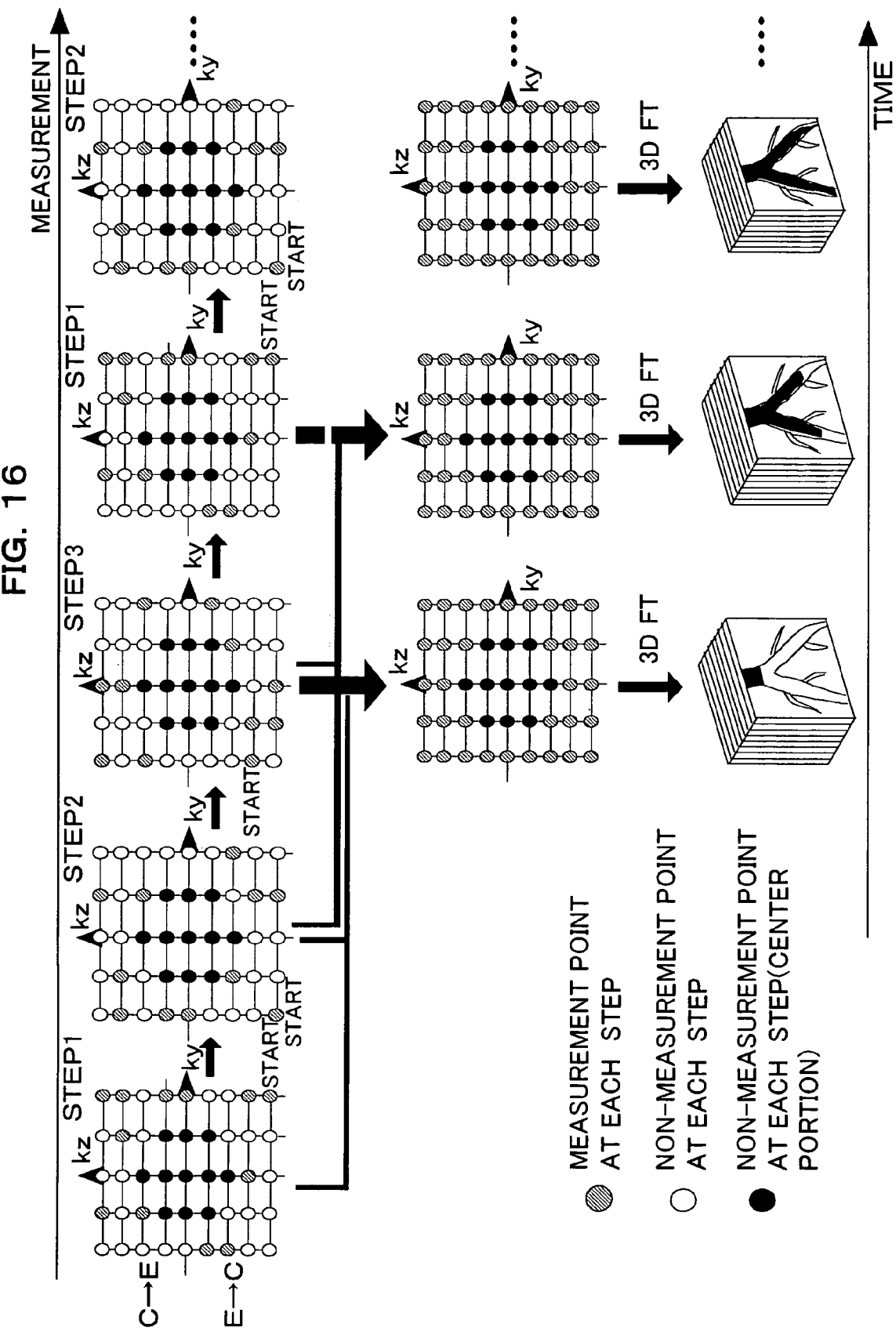
FIG. 16 is a diagram for explaining a measuring method in a first example of the second embodiment of the present invention.

At the first session of measurement, as illustrated in FIG. 16, at step 1, measurement is made for eleven sampling points of the essential measurement region (sampling points shown by the black circles in FIG. 15A) and for a group of the sampling points shown by the hatched circles in FIG. 15A (hereinafter refereed to a group a) thereby to collect data of the sampling points of the essential measurement region and the twelve sampling points of the peripheral measurement region.

Next, at step 2 illustrated in FIG. 16, measurement is made in eleven sampling points of the essential measurement and for a group of the sampling points shown by the hatched circles in FIG. 15B (hereinafter refereed to a group b) thereby to collect data of the sampling points of the essential measurement region and the eleven sampling points of the group b different from the group a of the peripheral measurement region.

Further, at step 3 in FIG. 16, data is collected for the eleven sampling points of the essential measurement region and eleven sampling points other than the groups a and b of the peripheral measurement region, that is, a group of the sampling points shown by the hatched lines in FIG. 15C.

Since all the data of the peripheral measurement region is obtained through the three times of sessions of measurement at steps 1, 2 and 3, an image is reconstructed by using the data of the entire region of the k space.

A three-dimensional Fourier transform is performed on the three-dimensional k-space to produce three-dimensional image data which is then projected to provide a two-dimensional image.

In a fourth session of measurement, like the first measurement (step 1), measurement is made in the essential measurement region and the group a thereby to obtain the data of the essential measurement region and a part of the peripheral measurement region. Data of the peripheral measurement region not having been obtained in the fourth measurement is prepared by using the data of the peripheral measurement region having been obtained in the second and the third sessions of measurement thereby to form three-dimensional data filled with the data of the entirety of the peripheral measurement region. Then, an image is reconstructed by using this three-dimensional data.

In each session on and after the fifth session of measurement, in the similar manner, three-dimensional data is prepared by using data of the essential measurement region obtained in this session, data of a part of the peripheral measurement region and data of the peripheral measurement region obtained in the most recent past two sessions of measurement. Then, an image is reconstructed by using this three-dimensional data.

According to such a measurement method, a time period required for a single session of measurement can be shortened to a large extent as compared with the case where data of the entire region of the k-space is measured (about ½ as compared with the aforesaid U.S. Patent), whereby an image can be reconstructed with the same interval as the time period required for a single session of measurement. Thus, the temporal resolution of an image displayed by the dynamic MRA imaging operation can be improved.

Further, since an image (that is, an image to be updated) is formed by using data of the entire region of the k-space, the degradation of an image can be prevented at a high-frequency region as well as a low-frequency region.

Since data at a low-frequency always contains data of all the sampling points within that region, a blood flow image with a high contrast can be obtained.

Further, the peripheral measurement region is divided into plural groups such that the sampling points in each of the groups are distributed so as not to be clustered spatially from one another and the respective groups have almost same sampling points. Thus, pulsation components of data is suppressed between succeeding sessions of measurement and so measurement can be performed stably.

Next, the explanation will be made as to the measuring order of sampling points.

As the measuring order of the k-space, there are knows the centric order, the sequential order etc. Any one of these orders may be employed in the second embodiment of the present invention.

In an example illustrated in FIG. 16, measuring order of sampling points is determined depending on the distance of a sampling point from the origin. That is, in the example illustrated in FIG. 16, first, the k-space is divided into two regions along the ky-axis or the kz-axis. In one of these two regions (e.g., an E-C region on the lower side in the figure), the measuring order is sorted in the order of sampling point having a longer distance from the origin, whist in the other region (e.g., a C-E region on the upper side in the figure), the measuring order is sorted in the order of sampling point having a shorter distance from the origin.

After the measuring order is sorted in this manner, measurement is started from a sampling point closest to the origin of the E-C region, then measurement of the sampling points is proceeded in the sorted measuring order, and measurement is terminated at the sampling point most away from the origin.

As explained above, the measurement of a sampling points means that the pulse sequence illustrated in FIG. 2, for example, is executed at a slice encode gradient magnetic field intensity or a phase encode gradient magnetic field intensity corresponding to the coordinate (ky, kz) of the sampling point.

Such a measuring order is same in each of the different groups. According to such a measuring order, the data at the low frequency region can be measured in a relatively wide time range including intermediate time points from the start to termination of measurement. Thus, the measuring timing can advantageously be adjusted easily such that the low frequency region is measured at a time point where the concentration of the contrast medium at a target blood vessel is most high.

Accordingly, an image of a target blood vessel can be drawn with a high contrast.

Figure 17:
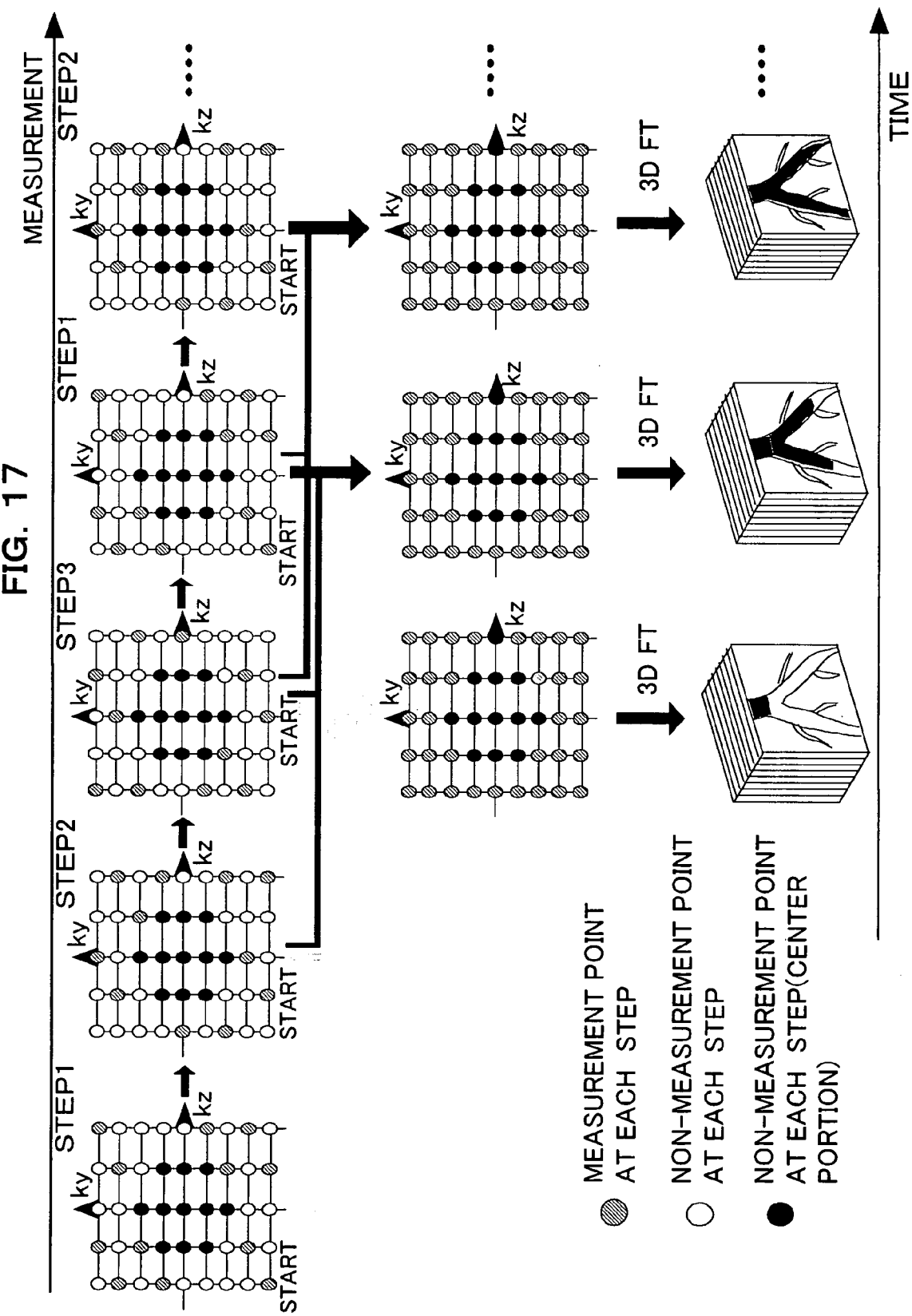
FIG. 17 is a diagram for explaining a measuring method in a second example of the second embodiment of the present invention.

In this respect, the measuring method according to the second embodiment is not limited to the aforesaid measuring order. For example, as illustrated in FIG. 17, measurement may be performed in such a sequential order that measurement is started from a sampling point at the left lowest corner, then measurement proceeds sequentially one point by one point to the right side end, then proceeds to an adjacent right-above point along the kz-axis, then proceeds sequentially one point by one point to the left side end.

In this second embodiment, also as illustrated in FIGS. 9A and 12A, a non-measurement region may be set.

Further, in this second embodiment, the peripheral measurement region is divided into the plural groups such that the sampling points in each of the groups are distributed so as not to be clustered spatially from one another and the respective groups have almost same sampling points. There are various kinds of such a setting method of the sampling points.

For example, the sampling points may be set in a manner that sum of squares of the distances from the origin to the respective sampling points is almost same in each of the groups and the sampling points are distributed uniformly within each group.

Next, description will be made on the third embodiment of the present invention.

According to the third embodiment, as an example, a peripheral measurement region is further divided in to a low and intermediate frequency region and a high frequency region and sampling points within each of these regions are divided into groups within each of which the sampling points are distributed uniformly in space.

Figure 18:
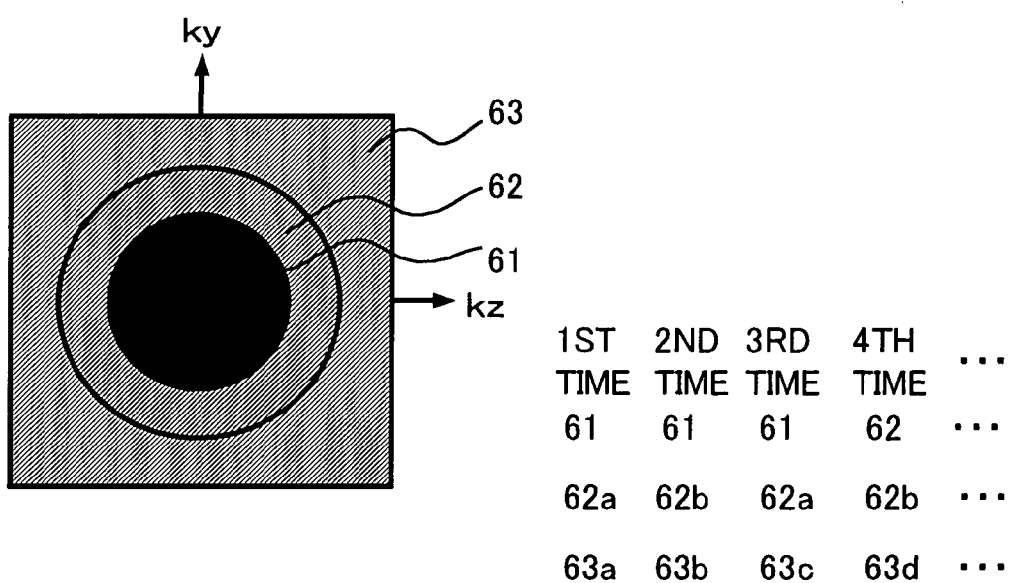
FIG. 18 is a diagram for explaining a measuring method in the third embodiment of the present invention.

That is, as illustrated in FIG. 18, the k-space is divided into an essential measurement region 61 of a low frequency region containing the origin, a low and intermediate frequency region 62 provided at the outside of the essential measurement region and a high frequency region 63 provided at the outside of the low and intermediate frequency region. The respective regions 61, 62 and 63 are mutually exclusive regions and so do not overlap from one another.

The essential measurement region 61 is a region to be measured at each session of measurement, like the second embodiment. Each of the low and intermediate frequency region 62 and the high frequency region 63 is divided into plural groups within each of which the sampling points are distributed uniformly in space. In each of these regions, the groups are sequentially measured one by one in each session of measurement.

In this case, the number of groups differs between the low and intermediate frequency region 62 and the high frequency region 63 in a manner that, for example, the low and intermediate frequency region 62 is formed by two groups a and b, and the high frequency region is formed by four groups a to d. This is synonymous that, supposing that the density of the sampling points measured at a single session of measurement is 1 in the essential measurement region 61, the density becomes ½ thereof in the low and intermediate frequency region 62 and becomes ¼ in the high frequency region 63.

In this case, in the first session of measurement, measurement is made in the essential measurement region 61, the group a of the low and intermediate frequency region 62 and the group a of the high frequency region 63. In the next session of measurement, measurement is made in the essential measurement region 61, the group b of the low and intermediate frequency region 62 and the group b of the high frequency region 63. In the third session of measurement, measurement is made in the essential measurement region 61, the group a of the low and intermediate frequency region 62 and the group c of the high frequency region 63. In the fourth session of measurement, measurement is made in the essential measurement region 61, the group b of the low and intermediate frequency region 62 and the group d of the high frequency region 63.

In this manner, in each of the low and intermediate frequency region 62 and the high frequency region 63, the groups thereof are sequentially measured cyclically.

In the forth session of measurement at which the measurement of the high frequency region 63 is completed, data for filling the three-dimensional k-space is obtained and an image is reconstructed by using the three-dimensional data.

Hereinafter, in each session of measurement, the three-dimensional data is prepared by using data measured at this session and data which is not measured at this session but measured in the past measurement, and an image is reconstructed by using the three-dimensional data.

In the third embodiment, as illustrated in FIG. 16, the measuring order of the sampling points may be sorted in accordance with the distance from the origin in each of the E-C region and the C-E region thereby to perform measurement in accordance with the sorted order. Alternatively, measurement may be performed in the sequential order as illustrated in FIG. 17.

In the third embodiment, also like the second embodiment, a time period required for a single session of measurement can be shortened and temporal resolution of an image can be improved. At this time, deterioration of an image can be prevented in the high frequency region as well as the low frequency region.

Further, in the third embodiment, since the peripheral measurement region is divided into two regions, a target blood vessel can be drawn with a high contrast in accordance with the thickness of the blood vessel.

Incidentally, the number of division of the peripheral measurement region and the density of the sampling points of the groups obtained through the division of the peripheral measurement region may be changed arbitrarily according to an object of the imaging Further, according to the third embodiment, the peripheral measurement region is divided into plural groups within each of which the sampling points are distributed uniformly in space, like the second embodiment. The third embodiment may be applied to a case where the peripheral measurement region is divided into plural regions like the first embodiment.

Incidentally, the method of displaying an image and the method of preparing a two-dimensional projection image from three-dimensional image data can be realized by using the known method described in the first embodiment.

Further, the three-dimensional data may be projected in an arbitrary direction such as a direction of a coronal section, a sagittal section, or axial traverse by using the optical shaft locus method such as the MIP, the Min IP etc. thereby to form and display a two-dimensional image. In this case, two-dimensional images may be sequentially generated while the projecting direction is rotated about a certain axis, and they may be connected to generate a moving image.

Further, the well-known rendering method may be employed such as the surface rendering, the volume rendering etc.

Although each of the aforesaid examples is explained as to the case where the boundary between the essential measurement region and the peripheral measurement region is set in the ky-kz direction, the boundary between the essential measurement region and the peripheral measurement region may be set in an arbitrary direction among the kx, ky and kz directions, in the combination of arbitrary two directions, or in each of these three directions.

Further, although each of the aforesaid examples is explained as to the case where the three-dimensional measurement is performed by phase-encoding in the z-and y-directions, the present invention is also applied to a case where the three-dimensional measurement is performed by phase-encoding positions of the z-direction through the combination of the slice selection gradient magnetic field and the RF pulses.

Further, although each of the aforesaid examples is explained as to the case of performing the three-dimensional measurement, the present invention is also applied to a case of performing the two-dimensional measurement (measurement at each slice) by setting the boundary between the essential measurement region and the peripheral measurement region in the kx-ky direction.

Further, the MRI apparatus and the measuring method using the apparatus according to the present invention is applied not only to the dynamic MRA using contrast agent but also to a case where arbitrary repetition measurement is performed in the MRI in the similar manner.

The numbers of the peripheral measurement regions or the groups of the peripheral measurement region in the aforesaid embodiments are merely examples and may be set arbitrarily according to the use and object of the invention.

In the aforesaid embodiments, for regions in the three-dimensional k-space which were not measured in each session of measurement, data is acquired through a diversion from the result of measurement in the session which is the closest past session in which the regions in the three-dimensional k-space, which were not measured in that session, had been measured. As another method, data of a part of the three-dimensional k-space which was not measured in a session of measurement may be generated through the interpolation of the two results of measurement in the session which is the closest past two sessions in which the portion in the three-dimensional k-space, which were not measured in that session, had been measured.

Further, in the aforesaid example, the essential measurement region is set at the center region. However, the essential measurement region may not necessarily be set at the center region but may be set at a peripheral region or a corner region and the center region may be divided into plural regions or groups so that the respective regions and the groups are measured at each session of measurement.

Thus, since the peripheral measurement region is not limited to the periphery of the center region, the peripheral measurement region can be defined as a divided measurement region.

INDUSTRIAL APPLICABILITY

According to the present invention, the measuring method can be realized which can reduce a measuring time in each session without significantly deteriorating the temporal resolution in a high frequency range when imaging is repeatedly performed in the MRI. Further, in such a measuring method, the direction dependency from the result of measurement can be eliminated

The invention claimed is:

1. In a measuring method in a magnetic resonance imaging apparatus which repeatedly measures an object to be examined by utilizing a nuclear magnetic resonance phenomenon, the method comprising:
a region setting step of setting, in a measuring space of the object (1), an essential measurement region (41, 61, 71, 81, 111, 131) and a divided measurement region (42, 62, 63, 72, 82, 112, 132) including plural divided portions which do not have any region overlapped with the essential measurement region;
a preceding measuring step of combining the essential measurement region with a selected divided portion of the plural divided portions of the divided measurement region to measure a nuclear magnetic resonance signal from the object as data of the measuring space;
a data generating step of combining the essential measurement region with the divided portion having not been selected in the preceding measuring step to measure a nuclear magnetic resonance signal from the object as data of the measuring space; sequentially combining the essential measurement region with the divided portion having not been measured in a preceding measuring step to measure a nuclear magnetic resonance signal from the object;
supplementing the data of the essential measurement region and the data of the divided portion thus measured with the data of the divided portion measured in the preceding measuring step to generate data of the measuring space; and
a step of generating an image of the object based on the measuring space generated in the data generating step.

2. In a measuring method in a magnetic resonance imaging apparatus which repeatedly measures an object to be examined by utilizing a nuclear magnetic resonance phenomenon, the method comprising:
a region setting step of setting, in a measuring space of the object (1), an essential measurement region (41, 61, 71, 81, 111, 131) having a center region of the measuring space and a plurality of peripheral measurement regions (42, 62, 63, 72, 82, 112, 132) which do not have any region overlapped with the essential measurement region;
a preceding measuring step of combining the essential measurement region with a selected peripheral portion of the plurality of the peripheral measurement regions to measure a nuclear magnetic resonance signal from the object as data of the measuring space;
a data generating step of combining the essential measurement region with the peripheral measurement region of the plurality of the peripheral measurement regions which has not been selected in the preceding measuring step to measure a nuclear magnetic resonance signal from the object as data of the measuring space; sequentially combining the essential measurement region with the peripheral measurement region having not been measured in a preceding measuring step to measure a nuclear magnetic resonance signal from the object; and supplementing the data of the essential measurement region and the data of the peripheral measurement region thus measured with the data of the peripheral measurement region measured in the preceding measuring step to generate data of the measuring space; and
a step of generating an image of the object based on the measuring space generated in the data generating step.

3. A measuring method in a magnetic resonance imaging apparatus according to claim 2, wherein the measuring space is a three-dimensional space, and a boundary line between the essential measurement region and the respective peripheral measurement regions in the entire three-dimensional measuring space is a line which divides the entire three-dimensional measuring space in at least two dimensional coordinate axis directions of three-dimensional coordinate axes which define the measuring space.

4. A measuring method in a magnetic resonance imaging apparatus according to claim 2 or 3, wherein the measuring space includes a non-measurement region (73, 83, 113) which is not being measured and does not overlap with the essential measurement region and the plurality of peripheral measurement regions.

5. A measuring method in a magnetic resonance imaging apparatus according to claim 2 or 3, wherein the region setting step changes a number of the division of the peripheral measurement region after executing the preceding measuring step and the data generating step for a predetermined number of times.

6. In a measuring method in a magnetic resonance imaging apparatus which repeatedly measures an object to be examined by utilizing a nuclear magnetic resonance phenomenon, the method comprising:
   a region setting step of setting, in a measuring space of the object (1), an essential measurement region (41, 61, 71, 81, 111, 131) having a center region of the measuring space and a peripheral measurement region (42, 62, 63, 72, 82, 112, 132) which does not have any region overlapped with the essential measurement region;
   a dividing step of diving a plurality of measuring sampling portions of the peripheral measurement region into a plurality of sampling groups which are distributed almost uniformly in the space;
   a preceding measuring step of combining the essential measurement region with a selected sampling group of the plurality of the plurality of sampling groups to measure a nuclear magnetic resonance signal from the object as data of the measuring space;
   a data generating step of combining the essential measurement region with the sampling group of the plurality of the sampling groups which has not been selected in the preceding measuring step to measure a nuclear magnetic resonance signal from the object as data of the measuring space; sequentially combining the essential measurement region with the sampling group having not been measured in a preceding measuring step to measure a nuclear magnetic resonance signal from the object; and supplementing the data of the essential measurement region and the data of the sampling group thus measured with the data of the sampling group measured in the preceding measuring step to generate data of the measuring space; and
   a step of generating an image of the object based on the measuring space generated in the data generating step.

7. A measuring method in a magnetic resonance imaging apparatus according to claim 6, wherein the measuring space is a three-dimensional space, and a boundary line between the essential measurement region and the respective sampling groups in the entire three-dimensional measuring space is a line which divides the entire three-dimensional measuring space into the region and the groups in at least two dimensional coordinate axis directions of three-dimensional coordinate axes which define the measuring space.

8. A measuring method in a magnetic resonance imaging apparatus according to claim 6 or 7, wherein the measuring space includes a non-measurement region (73, 83, 113) which is not being measured and does not overlap with the essential measurement region and the plurality of sampling groups.

9. A measuring method in a magnetic resonance imaging apparatus according to claim 6, wherein the region setting step changes a divided number of the plurality of sampling groups after executing the preceding measuring step and the data generating step for a predetermined number of times.

10. A magnetic resonance imaging apparatus which includes a nuclear magnetic resonance generation means for causing an object to be examined nuclear magnetic resonance, an encoding means for phase-encoding a nuclear magnetic resonance signal from the object, and an image reconstruction means for measuring the nuclear magnetic resonance signal and reconstructing an image of the object based on the nuclear magnetic resonance signal thus measured, the magnetic resonance imaging apparatus further comprising:
   a storage means (18, 19) which stores, as a measuring space of the object (1), an essential measurement region (41, 61, 71, 81, 111, 131) and a divided measurement region (42,62,63,72, 82, 112, 132) including plural divided portions which do not have any region overlapped with the essential measurement region; and
   a control means (8) which controls operations of the nuclear magnetic resonance generation means, the encoding means and the image reconstruction means to control measurement of the measuring space determined by phase encoding, and the control means further combines the essential measurement region stored in the storage means with a selected divided portion of the plural divided portions of the divided measurement region to measure a nuclear magnetic resonance signal from the object as data of the measuring space; combines the essential measurement region with the divided portion having not been measured in the preceding measurement to measure a nuclear magnetic resonance signal from the object as data of the measuring space; sequentially combines the essential measurement region with the divided portion having not been measured in a preceding measurement to measure a nuclear magnetic resonance signal from the object; and supplements the data of the essential measurement region and the data of the divided portion thus measured with the data of the divided portion measured in the preceding measurement to generate data of the measuring space and generates data of the measuring space.

11. A magnetic resonance imaging apparatus according to claim 10, wherein the essential measurement region is a center region of the measuring apace, and the divided measurement region is peripheral region of the center region.

12. A magnetic resonance imaging apparatus according to claim 11, wherein the peripheral region is divided into a plurality of sampling groups which are formed by dividing a plurality of measuring sampling portions almost uniformly in space distribution, and the plurality of sampling groups are set as the plurality of divided portions.

13. A measuring method in a magnetic resonance imaging apparatus according to claim 8, wherein the region setting step changes a divided number of the plurality of sampling groups after executing the preceding measuring step and the data generating step for a predetermined number of times.

14. A measuring method in a magnetic resonance imaging apparatus according to claim 3, wherein said boundary line is an asymmetric line in respect to at least one direction of said two dimensional coordinate axis directions.

15. A measuring method in a magnetic resonance imaging apparatus according to claim 3, wherein said essential measurement region is a quadrangle region of center region in said measuring space, said peripheral measurement regions being divided into four regions at peripheral of said essential measurement region.

16. A measuring method in a magnetic resonance imaging apparatus according to claim 3, wherein said measuring space is divided into nine quadrangle regions, said essential measurement region being center region in said nine quadrangle regions, said peripheral measurement regions being four regions in said nine quadrangle regions, said four regions each of which contacts to one side of said essential measurement region.

17. A measuring method in a magnetic resonance imaging apparatus according to claim 3, wherein said measuring space is divided into a circle region and an outside region outside of said circle region, said essential measurement region being a quadrangle region in center region of said circle regions, said peripheral measurement regions being four regions in said circle region, said peripheral measurement regions at peripheral of said essential measurement region.

18. A measuring method in a magnetic resonance imaging apparatus according to claim 17, wherein a scanning of said essential measurement region and peripheral measurement regions is performed spirally.

19. A measuring method in a magnetic resonance imaging apparatus according to claim 17, wherein a scanning of said essential measurement region and peripheral measurement regions is performed spirally, said scanning being started from a portion most away from an origin until a scanning point reaches said origin, being started from a portion closest to said origin after the scanning point reaches said origin.

20. A measuring method in a magnetic resonance imaging apparatus according to claim 3, wherein said measuring space is divided into a second circle region and an outside region outside of said second circle region, said essential measurement region being a first circle region in a center region of said second circle region, said peripheral measurement regions being four regions in said second circle region, said peripheral measurement regions at peripheral of said essential measurement region.

21. A measuring method in a magnetic resonance imaging apparatus according to claim 20, wherein a scanning of said essential measurement region and peripheral measurement regions is performed spirally, said scanning being started from a portion most away from an origin until a scanning point reaches said origin, being started from a portion closest to said origin after the scanning point reaches said origin.

22. A magnetic resonance imaging apparatus according to claim 12, wherein said sampling groups of said peripheral measuring region are a first group, second group and third group, said sampling points of said essential measurement region and said first group being measured, said sample points of said essential measurement region and said second group being measured, said sample points of said essential measurement region and said third group being measured, an image being reconstructed by using sample points of said essential measurement region and said peripheral region, measuring order of said sampling points being determined depending on a distance of a sampling point from an origin of said measuring space.

23. A magnetic resonance imaging apparatus according to claim 12, wherein said sampling groups of said peripheral measuring region are a first group, second group and third group, said sampling points of said essential measurement region and said first group being measured, said sample points of said essential measurement region and said second group being measured, said sample points of said essential measurement region and said third group being measured, an image being reconstructed by using sample points of said essential measurement region and said peripheral region, measuring order of said sampling points being determined depending on a sequential order.

* * * * *